US008871780B2

(12) United States Patent
Mickle et al.

(10) Patent No.: US 8,871,780 B2
(45) Date of Patent: Oct. 28, 2014

(54) PHENYLETHANOIC ACID, PHENYLPROPANOIC ACID AND PHENYLPROPENOIC ACID CONJUGATES AND PRODRUGS OF HYDROCODONE, METHOD OF MAKING AND USE THEREOF

(75) Inventors: Travis Mickle, Coralville, IA (US); Sven Guenther, Coralville, IA (US); Christal Mickle, Coralville, IA (US); Guochen Chi, North Liberty, IA (US); Jaroslaw Kanski, Blacksburg, VA (US); Andrea K. Martin, Fincastle, VA (US); Bindu Bera, Blacksburg, VA (US)

(73) Assignee: KemPharm, Inc., Coralville, IA (US)

( * ) Notice: Subject to any disclaimer, the term of this patent is extended or adjusted under 35 U.S.C. 154(b) by 645 days.

(21) Appl. No.: 12/828,456

(22) Filed: Jul. 1, 2010

(65) Prior Publication Data

US 2011/0002991 A1 Jan. 6, 2011

Related U.S. Application Data

(60) Provisional application No. 61/222,730, filed on Jul. 2, 2009.

(51) Int. Cl.
*A61K 31/485* (2006.01)
*A61K 45/06* (2006.01)
*A61K 47/48* (2006.01)

(52) U.S. Cl.
CPC .................. *A61K 47/48038* (2013.01)
USPC ........................ 514/282; 514/557; 514/160

(58) Field of Classification Search
USPC .......................................... 514/282, 161, 557
See application file for complete search history.

(56) References Cited

U.S. PATENT DOCUMENTS

| 1,731,152 | A | 10/1929 | Schopf |
|---|---|---|---|
| 7,375,082 | B2 | 5/2008 | Mickle et al. |
| 7,375,083 | B2 | 5/2008 | Mickle et al. |
| 8,461,137 | B2 | 6/2013 | Mickle et al. |
| 2005/0176646 | A1 | 8/2005 | Mickle et al. |
| 2006/0167258 | A1 | 7/2006 | Likhotvorik et al. |
| 2008/0090771 | A1* | 4/2008 | Moncrief ........................ 514/17 |
| 2008/0132570 | A1 | 6/2008 | Xiang |
| 2009/0156820 | A1 | 6/2009 | Wang et al. |
| 2011/0002990 | A1 | 1/2011 | Mickle et al. |
| 2012/0142719 | A1 | 6/2012 | Mickle et al. |
| 2012/0142720 | A1 | 6/2012 | Mickle et al. |
| 2013/0245265 | A1 | 9/2013 | Mickle et al. |
| 2013/0252994 | A1 | 9/2013 | Mickle et al. |
| 2013/0259909 | A1 | 10/2013 | Mickle et al. |

FOREIGN PATENT DOCUMENTS

| EA | 8864 B1 | 8/2007 |
|---|---|---|
| GB | 320749 | 10/1920 |
| RU | EA 08864 | 8/2007 |
| WO | 92/08459 | 5/1991 |
| WO | 96/16063 | 5/1996 |
| WO | WO96/16063 | * 5/1996 |
| WO | WO 2005/032474 | 4/2005 |
| WO | 2011002991 | 1/2011 |

OTHER PUBLICATIONS

Persson-Stubberud et al. Separation of ibufprofen, codeine phosphate, their degradation products and impurities by capillary electrophoresis I. Method development and optimization with fractional factorial design J. of Chromatogrphy A, 798 (1998) pp. 307-314.*
International Search Report in PCT/US2010/040775, dated Aug. 16, 2010.
Bertram, F. and W. Stoltenberg, "Kinische Erfahrungen MIT Acedicon," Klinische Wochenschrift, 8, Jahrgang, Nr. 19, 1929, pp. 883-886.
Bradford, L.W. and J.W. Brackett, "Systematic Procedure for the Identification of Dangerous Drugs, Poisons, and Narcotics by Ultraviolet Spectrophotometry," Laboratory of Criminalistics, 1956, pp. 353-382.
Catlin, D.H., "Analytical Chemistry and the Games of the XXIIIrd Olympiad in Los Angelos, 1984," Clin. Chem., 1987, pp. 319-327.
Fischer, R. and M.S. Karawia, "Zum Nachweis von Analgeticis und Alkaloiden Mittels Tetraphenylbornatrium (Kalignost) und Nitrokorpern," Aus dem Pharmakognostischen Institut der Universitat Graz, 1953, pp. 366-374.
Hosztafi, S., Köhegyi, I., Simon, C., Fürst, Z., "Synthesis and Analgetic Activity of Nicotinic Esters of Morphine Derivatives" Arzneimittel-Forschung [1993, 43(11):1200-1203].
Hydrocodone chemical structure (ChemSpider, last visit Sep. 18, 2013).
Jane, I., A. McKinnon, and R.J. Flanagan, "High-Performance Liquid Chromatographic Analysis of Basic Drugs on Silica Columns Using Non-Aqueous Ionic Eluents. II. Application of UV, Flourescence and Electrochemical Oxidation detection," Journal of Chromotography, 1985, pp. 191-225.
Leland, D.L. J.O. Polazzi and M.P.Kotick, "Preparation of 7-beta-Methyldihydrothebaine," J. Org . Chem., 1980, pp. 4026-4028.
Micheel, F. and W. Leifels, "Papierchromatographische Trennungen von Alkaloidgemischen an Succinylzellulose-Papieren," Aus dem Organisch-chemischen Institute der Universitate Munster, 1960.
Perrigo et al., "Use of Dual-col. Fused-Silica Capillary Gas Chromatography in Combination with Detector Response Factors for Analytical Toxicology," Journal of Chromatography, 1985 pp. 81-88.
Small, L., H.M. Fitch and W.E. Smith, "The Addition of Organomagnesium Halides to Pseudocodeine Types. II. Preparation of Nuclear Alkylated Morphine Derivatives," Preparation of Nuclear Alkylated Morphine Derivatives, J. Am. Chem. Soc., 1936, pp. 1457-1463.
Small, L., S. G. Turnbull, and H.M. Fitch, "The Addition of Organomagnesium Halides to Pseudocodiene Types. IV. Nuclear-Substituted Morphine Derivatives," J. Org . Chem., 1938, pp. 204-232.
Thebacon —List of Thebacon suppliers; SciFinder Scholar, Report for CAS RN 466-90-0, 2011.
Von Ernst Vidic, "Eine neue Schnellmethode zur Untersuchung von Urin auf Opiate und deren Derivate," Aus den institut fur gerichtliche und soziale Medizin der Freien Universitat Berlin, 1951.
International Search Report in PCT/US2010/040785, dated Aug. 20, 2010.

(Continued)

*Primary Examiner* — Jennifer M Kim
(74) *Attorney, Agent, or Firm* — McAndrews, Held & Malloy, Ltd.

(57) ABSTRACT

The presently described technology provides phenylethanoic acid, phenylpropanoic acid, phenylpropenoic acid, a salt thereof, a derivative thereof or a combination thereof chemically conjugated to hydrocodone (morphinan-6-one, 4,5-alpha-epoxy-3-methoxy-17-methyl) to form novel prodrugs or compositions of hydrocodone which have a decreased potential for abuse of hydrocodone. The present technology also provides methods of treating patients, pharmaceutical kits and methods of synthesizing conjugates of the present technology.

10 Claims, 11 Drawing Sheets

(56) References Cited

OTHER PUBLICATIONS

Office Action in U.S. Appl. No. 12/828,381, dated Aug. 1, 2012.
Office Action in U.S. Appl. No. 12/828,381, dated Nov. 8, 2012.
Office Action in U.S. Appl. No. 13/378,857, dated Feb. 22, 2013.
Notice of Allowance in U.S. Appl. No. 12/828,381, dated Mar. 25, 2013.
Office Action in U.S. Appl. No. 13/378,857, dated May 23, 2013.
Office Action in U.S. Appl. No. 13/888,578, dated Jul. 2, 2013.
Office Action in U.S. Appl. No. 13/888,583, dated Aug. 2, 2013.
Notice of Allowance in U.S. Appl. No. 13/888,578, dated Sep. 4, 2013.
Office Action in U.S. Appl. No. 13/788,800, dated Sep. 19, 2013.
Office Action in U.S. Appl. No. 13/378,857, dated Sep. 25, 2013.

\* cited by examiner

FIGURE 1

Structures of some phenylethanoic acids and derivatives

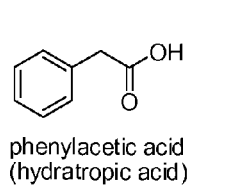
phenylacetic acid
(hydratropic acid)

2-hydroxyphenyl-
acetic acid

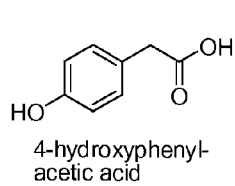
4-hydroxyphenyl-
acetic acid

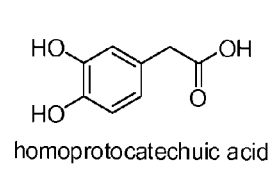
homoprotocatechuic acid

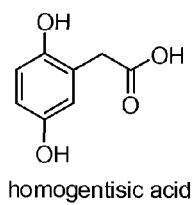
homogentisic acid

2,6-dihydroxy-
phenylacetic acid

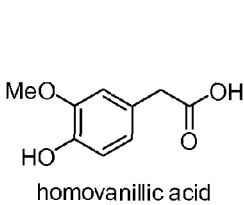
homovanillic acid

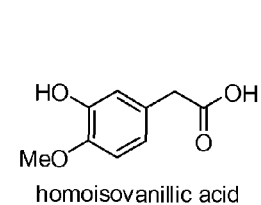
homoisovanillic acid

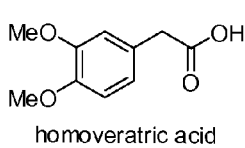
homoveratric acid

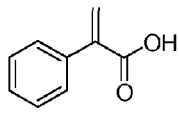
atropic acid

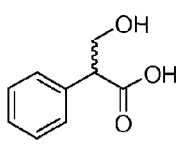
tropic acid

diclofenac

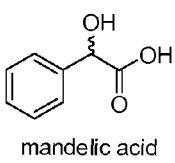
mandelic acid

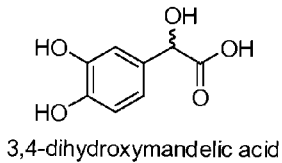
3,4-dihydroxymandelic acid

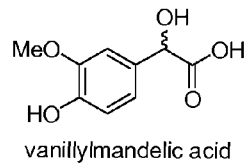
vanillylmandelic acid

isovanillylmandelic acid

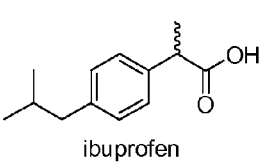
ibuprofen

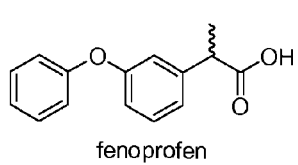
fenoprofen

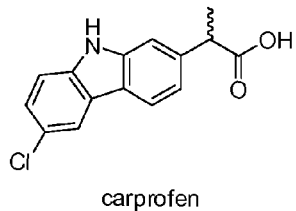
carprofen flurbiprofen    ketoprofen    naproxen

Structures of exemplar phenylpropanoic acids and derivatives

Structures of some phenylpropenoic acids and derivatives

FIGURE 4

4A. Common hydrocodone products and dosage ranges

| Second API | | Hydrocodone Bitartrate |
|---|---|---|
| Name | Strength | Strength[a] |
| acetaminophen | 300 mg | 5 mg |
| | | 7.5 mg |
| | | 10 mg |
| | 325 mg | 5 mg |
| | | 7.5 mg |
| | | 10 mg |
| | 400 mg | 5 mg |
| | | 7.5 mg |
| | | 10 mg |
| | 500 mg | 2.5 mg |
| | | 5 mg |
| | | 7.5 mg |
| | | 10 mg |
| | 650 mg | 7.5 mg |
| | | 10 mg |
| | 660 mg | 10 mg |
| | 750 mg | 7.5 mg |
| | | 10 mg |
| ibuprofen | 200 mg | 2.5 mg |
| | | 7.5 mg |
| | | 10 mg |
| aspirin | 500 mg | 2.5 mg |
| | | 5 mg |
| | | 7.5 mg |
| chlorpheniramine maleate | 2 mg | 5 mg |
| | 4 mg | |
| | 8 mg | 10 mg |
| phenylpropanolamine hydrochloride | 12.5 mg | 2.5 mg |
| | 25 mg | 5 mg |
| phenylephrine hydrochloride | 5 mg | 1.66 mg |
| | 10 mg | 3.75 mg |
| pseudoephedrine hydrochloride | 60 mg | 5 mg |
| phenylephrine hydrochloride | 5 mg | 1.66 mg |
| | | 3.75 mg |
| guaifenesin | 100 mg | 5 mg |
| | 300 mg | |

FIGURE 4 (continued)

4B. Common hydrocodone products and dosage ranges (continued)

| Hydrocodone Bitartrate | Second API | | Third API | |
|---|---|---|---|---|
| Strength[a] | Name | Strength | Name | Strength |
| 5 mg | homatropine methylbromide | 1.5 mg | na | |
| 2.5-10 mg | acetaminophen | 300-750 mg | na | |
| 2.5-10 mg | ibuprofen | 200 mg | na | |
| 5-10 mg | chlorpheniramine maleate | 4-8 mg | na | |
| 2.5-7.5 mg | aspirin | 500 mg | na | |
| 2.5-5 mg | phenylpropanolamine hydrochloride | 12.5-25 mg | na | |
| 1.66-3.75 mg | phenylephrine hydrochloride | 5-10 mg | na | |
| 5 mg | pseudoephedrine hydrochloride | 60 mg | na | |
| 5 mg | guaifenesin | 100-300 mg | na | |
| 1.66-3.75 mg | phenylephrine hydrochloride | 5 mg | pyrilamine maleate | 8.33 mg |
| 5 mg | chlorpheniramine maleate | 2 mg | pseudoephedrine hydrochloride | 30 mg |

[a]Doses of hydrocodone prodrugs of this invention can be calculated from hydrocodone bitartrate (conversion formula was listed in previous invention disclosure document).

Oral PK Profiles (HC)
Ibu-HC vs. Cinnamate-HC vs. Hydrocodone·BT

Oral PK Profiles (HM)
Ibu-HC vs. Cinnamate-HC vs. Hydrocodone·BT

FIGURE 13
13A.
Synthesis of Hydrocodone-Ibuprofen
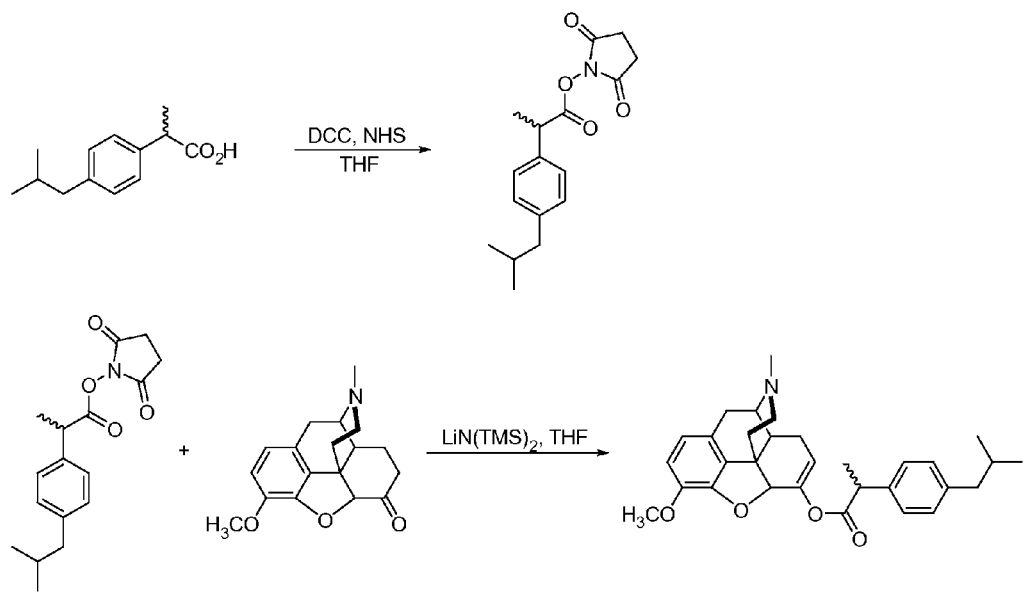
13B.
Synthesis of cinnamic acid ester of hydrocodone:
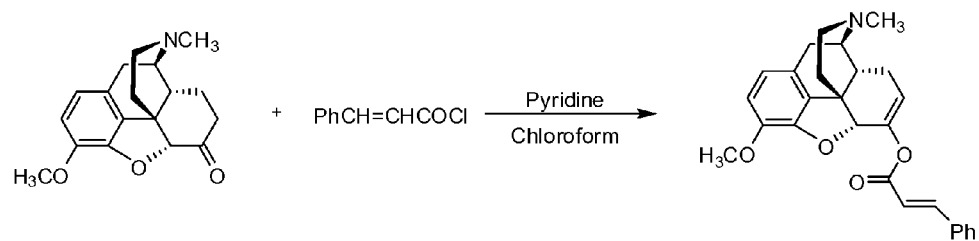

PHENYLETHANOIC ACID, PHENYLPROPANOIC ACID AND PHENYLPROPENOIC ACID CONJUGATES AND PRODRUGS OF HYDROCODONE, METHOD OF MAKING AND USE THEREOF

RELATED APPLICATIONS

This application claims the priority of U.S. provisional application Ser. No. 61/222,730, filed Jul. 2, 2009, which is incorporated by reference in its entirety.

FEDERALLY SPONSORED RESEARCH OR DEVELOPMENT

[Not Applicable]

BACKGROUND OF THE INVENTION

Opioids are highly effective as analgesics and are commonly prescribed for the treatment of acute and chronic pain. They are also commonly used as antitussives. The opioids, however, also produce euphoria and are highly addictive. As a result they are often abused with far reaching social and health related consequences.

Because of the inherent potential for abuse, it is desirable that any pharmaceutical composition containing an opioid agonist be made as abuse-resistant or abuse-deterrent as practical. Illicit users often will attempt to circumvent the extended release properties of these dosage forms by injecting or otherwise misusing the product in order to achieve an immediate release of the opioid agonist.

Despite their addictive properties and the potential for abuse, morphine-like drugs, particularly, codeine, hydrocodone, and oxycodone have been routinely prescribed as treatment for severe acute and chronic pain in recent decades. This is, in part, because there are no alternatives to relieve severe pain that is resistant to abuse potential except other less potent analgesics such as non-steroidal anti-inflammatory drugs (NSAIDS). In this regard, there has been work to decrease the abuse potential. Thus far, approaches taken, unfortunately, have not solved the problem. Therefore there is still a need for drug-abuse resistant compositions.

Hydrocodone is an opioid analgesic and antitussive and occurs as fine, white crystals or as crystalline powder. Hydrocodone is a semisynthetic narcotic analgesic prepared from codeine with multiple actions qualitatively similar to those of codeine. It is mainly used for relief of moderate to moderately severe pain. Additionally, it is used as an antitussive in cough syrups and tablets in sub-analgesic doses (2.5-5 mg).

Patients taking opioid analgesics such as hydrocodone for pain relief can become unintentionally addicted. As tolerance to the opioids develops, more drug is needed to alleviate the pain and generate the sense of well being initially achieved with the prescribed dose. This leads to dose escalation, which if left unchecked can lead rapidly to addiction. In some cases patients have become very addicted in as little as thirty days.

BRIEF SUMMARY OF THE INVENTION

The present technology utilizes covalent conjugation of the opioid hydrocodone with certain aryl carboxylic acids to decrease its potential for causing overdose or abuse, by requiring the active hydrocodone to be released through enzymatic or metabolic breakdown of the conjugate in vivo. The present technology also provides methods of delivering hydrocodone as conjugates that release the hydrocodone following oral administration while being resistant to abuse by circuitous routes such as intravenous ("shooting") injection and intranasal administration ("snorting").

The presently described technology in at least one aspect provides a slow or sustained or controlled release composition of conjugated hydrocodone that allows slow or sustained or controlled delivery of the hydrocodone and/or its active metabolite, hydromorphone, into the blood system of a human or animal within a safe therapeutic window upon, for example, oral administration. At least some compositions and formulations of the current technology can lessen addiction, abuse potential and/or other common side effects associated with hydrocodone and similar compounds.

In one aspect, the present technology provides a composition comprising at least one conjugate of hydrocodone and at least one of phenylethanoic acid, phenylpropanoic acid, phenylpropenoic acid, a salt thereof, a derivative thereof or a combination thereof.

In another aspect, the present technology provides a composition comprising at least one phenylethanoic acid, a salt thereof, a derivative thereof or a combination thereof having the formula I:

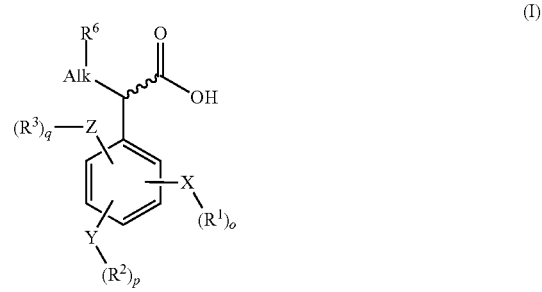

wherein, X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; Alk is an alkyl chain —$(CH_2)_n$— wherein n is 0 or 1; and $R^6$ is H, OH or carbonyl. In some aspects, the phenylethanoic acid is profen or tyrosine metabolite.

In another aspect, the present technology provides a composition comprising at least one conjugate of hydrocodone and at least one phenylethanoic acid, phenylpropanoic acid, phenylpropenoic acid, a salt thereof, a derivative thereof or a combination thereof, wherein the phenylpropenoic acid, phenylpropanoic acid, a salt thereof, a derivative thereof or a combination thereof having the formula II or formula III:

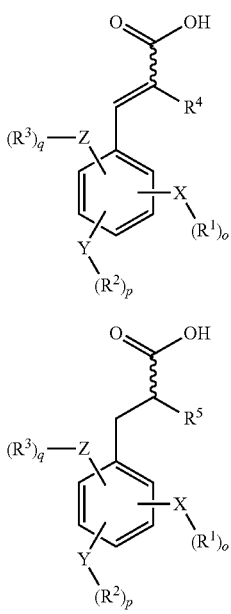

wherein, X, Y and Z are independently selected from the group consisting of H, O, S, NH and —(CH$_2$)$_x$—; R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; R$^4$ is H or OH; and R$^5$ is H, OH or carbonyl.

In some aspects, the prodrug or hydrocodone conjugate of the present technology is a phenylethanoate-hydrocodone conjugate, phenylpropanoate-hydrocodone conjugate, or a phenylpropenoate-hydrocodone conjugate.

In some aspects, the prodrug or hydrocodone conjugate of the present technology is ibuprofen-hydrocodone, cinnamate-hydrocodone or naproxen-hydrocodone.

In one aspect of the present technology, the prodrug or hydrocodone conjugate of the present technology is used to treat narcotic or opioid abuse or prevent opioid withdrawal.

In another aspect of the present technology, the prodrug or hydrocodone conjugate of the present technology is used to treat pain.

In another aspect of the present technology, the prodrug or hydrocodone conjugate of the present technology is used to treat moderate to severe pain.

In another aspect of the present technology, the prodrug or hydrocodone conjugate of the present technology reduces or prevents oral, intranasal or intravenous drug abuse.

In another aspect of the present technology, the prodrug or hydrocodone conjugate of the present technology provides oral, intranasal or parenteral drug abuse resistance.

In another aspect of the present technology, the prodrug or hydrocodone conjugate of the present technology provides a slower rate of release over time and a substantially equivalent AUC when compared to a molar equivalent amount of unconjugated hydrocodone over that same time period.

In another aspect of the present technology, the prodrug or hydrocodone conjugate of the present technology exhibits less variability in the oral PK profile when compared to unconjugated hydrocodone.

In another aspect, the prodrug or hydrocodone conjugate of the present technology has reduced side effects when compared with unconjugated hydrocodone.

In another aspect, the prodrug or hydrocodone conjugate of the present technology prevents drug tampering by either physical or chemical manipulation.

In another aspect, the prodrug or hydrocodone conjugate of the present technology is provided in an amount sufficient to provide a therapeutically bioequivalent AUC when compared to a molar equivalent of unconjugated hydrocodone. In other aspects of the present technology, the prodrug or hydrocodone conjugate is provided in an amount sufficient to provide a therapeutically bioequivalent AUC when compared to unconjugated hydrocodone but does provide a lower $C_{max}$ or does not provide a $C_{max}$ spike. In yet another aspect, the prodrug or hydrocodone conjugate is provided in an amount sufficient to provide a therapeutically bioequivalent AUC when compared to unconjugated hydrocodone, but does not provide an equivalent $C_{max}$ spike (for example, has a lower $C_{max}$). In some aspects, at least one conjugate provides a therapeutically bioequivalent Cmax when compared to unconjugated hydrocodone.

In another aspect of the present technology, the prodrug or hydrocodone conjugate exhibits less variability in the intranasal PK profile when compared to unconjugated hydrocodone. In yet another aspect, the prodrug or hydrocodone conjugate exhibits less variability in the parenteral PK profile when compared to unconjugated hydrocodone. In yet a further aspect, the prodrug or hydrocodone conjugate exhibits less variability in the intravenous PK profile when compared to a molar equivalent of unconjugated hydrocodone.

In a further aspect, the present technology provides a method for treating a patient having a disease, disorder or condition requiring binding of an opioid to the opioid receptors of the patient, comprising orally administering to the patient a pharmaceutically effective amount of at least one conjugate of hydrocodone and at least one of phenylethanoic acid, phenylpropanoic acid, phenylpropenoic acid, a salt thereof, a derivative thereof or a combination thereof.

In another aspect, the present technology provides a method for treating a patient having a disease, disorder or condition requiring or mediated by binding of an opioid to the opioid receptors of the patient, comprising orally administering to the patient a pharmaceutically effective amount of at least one conjugate of hydrocodone and at least one of phenylethanoic acid, phenylpropanoic acid, phenylpropenoic acid, wherein the conjugate of hydrocodone is ibuprofen-hydrocodone, cinnamate-hydrocodone or naproxen-hydrocodone.

In another aspect, the present technology provides a method for treating a patient having a disease, disorder or condition requiring inhibiting binding of an opioid to the opioid receptors of the patient, comprising orally administering to the patient a pharmaceutically effective amount of at least one conjugate of hydrocodone and at least one of phenylethanoic acid, phenylpropanoic acid, phenylpropenoic acid, a salt thereof, a derivative thereof or a combination thereof.

In yet another aspect, the present technology provides a method for treating a patient having a disease, disorder or condition requiring inhibiting binding of an opioid to the opioid receptors of the patient, comprising orally administering to the patient a pharmaceutically effective amount of at least one conjugate of hydrocodone and at least one of phenylethanoic acid, phenylpropanoic acid, phenylpropenoic acid, a salt thereof, a derivative thereof or a combination thereof, wherein the conjugate is ibuprofen-hydrocodone, cinnamate-hydrocodone, or naproxen-hydrocodone.

In yet another aspect, the present technology provides a pharmaceutical kit comprising a specified amount of individual doses in a package containing a pharmaceutically effective amount of at least one conjugate of hydrocodone and at least one of phenylethanoic acid, phenylpropanoic acid, phenylpropenoic acid, a salt thereof, a derivative thereof or a combination thereof.

In some aspects, the present technology provides a pharmaceutical kit including a conjugate of hydrocodone and at least one phenylethanoic acid, a salt thereof, a derivative thereof or a combination thereof having the formula I:

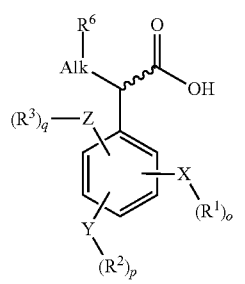

(I)

wherein, X, Y and Z are independently selected from the group consisting of H, O, S, NH and —(CH$_2$)$_x$—; R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; Alk is an alkyl chain —(CH$_2$)$_n$—, wherein n is 0 or 1; and R$^6$ is H, OH or carbonyl.

In another aspect, the present technology provides a pharmaceutical kit including a conjugate of hydrocodone and at least one of phenylpropenoic acid, phenylpropanoic acid, a salt thereof, a derivative thereof or a combination thereof having the formula II or formula III:

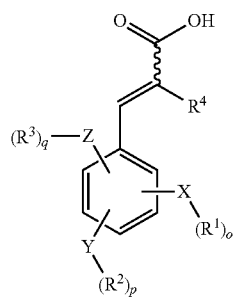

(II)

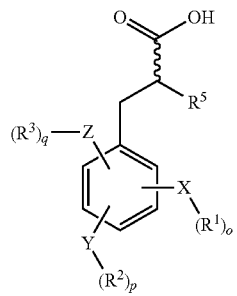

(III)

wherein, X, Y and Z are independently selected from the group consisting of H, O, S, NH and —(CH$_2$)$_x$—; R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; R$^4$ is H or OH; and R$^5$ is H, OH or carbonyl.

In some aspects, the kit includes instructions for use of the kit in a method for treating or preventing drug withdrawal symptoms or pain in a human.

In yet another aspect, the present technology provides a prodrug comprising at least one phenylethanoate hydrocodone conjugate, a salt thereof, a derivative thereof or a combination thereof, wherein the phenylethanoate is derived from phenylethanoate acid having the formula I:

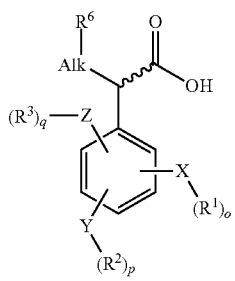

(I)

wherein, X, Y and Z are independently selected from the group consisting of H, O, S, NH and —(CH$_2$)$_x$—; R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; Alk is an alkyl chain —(CH$_2$)$_n$—, wherein n is 0 or 1; and R$^6$ is H, OH or carbonyl.

In another aspect, the present technology provides a prodrug comprising at least one phenylpropanoate hydrocodone conjugate, phenylpropenoate hydrocodone conjugate, a salt thereof, a derivative thereof or a combination thereof, wherein the phenylpropanoate or phenylpropenoate is of formula II or formula III:

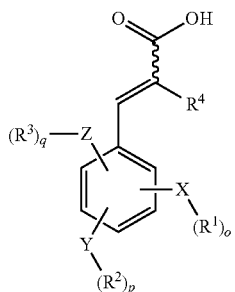

(II)

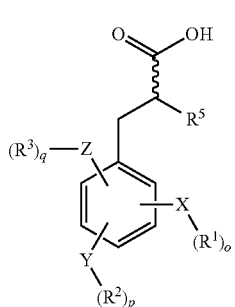

(III)

wherein, X, Y and Z are independently selected from the group consisting of H, O, S, NH and —$(CH_2)_x$—; $R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl; o, p, q are independently selected from 0 or 1; x is an integer between 1 and 10; $R^4$ is H or OH; and $R^5$ is H, OH or carbonyl.

In some aspects, the present technology provides a prodrug comprising ibuprofen-hydrocodone.

In other aspects, the present technology provides a prodrug comprising cinnamate-hydrocodone.

In other aspects, the present technology provides a prodrug comprising naproxen-hydrocodone.

BRIEF DESCRIPTION OF SEVERAL VIEWS OF THE DRAWINGS

FIG. 4. Common hydrocodone products and dosage ranges.

FIG. 13. Synthesis of exemplary conjugate compounds of the present technology.

DETAILED DESCRIPTION OF THE INVENTION

Figure 1:
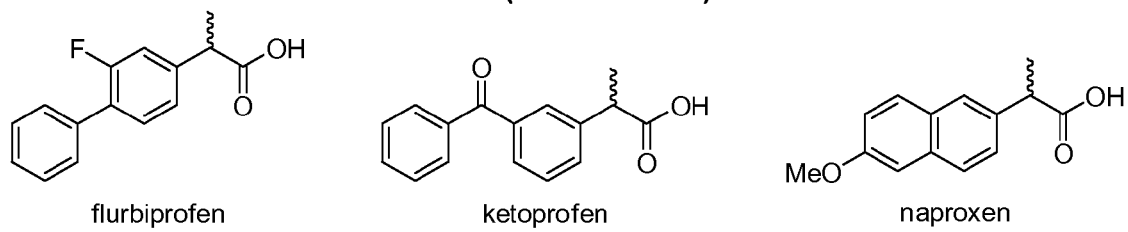
FIG. 1. Structures of some phenylethanoic acids and derivatives for use in making the conjugates of the present technology.

The present technology provides compositions comprising aryl carboxylic acids chemically conjugated to hydrocodone (morphinan-6-one, 4,5-alpha-epoxy-3-methoxy-17-methyl) to form novel prodrugs and compositions of hydrocodone. In some embodiments, the chemical bond between these two moieties can be established by reacting the C-6 enol tautomer of hydrocodone with the carboxylic acid function of an aryl carboxylic acid thereby creating an enol-ester conjugate.

The use of "opioid" is meant to include any drug that activates the opioid receptors found in the brain, spinal cord and gut. There are four broad classes of opioids: naturally occurring opium alkaloids, such as morphine (the prototypical opioid), codeine and thebaine; endogenous opioid peptides, such as endorphins; semi-synthetics such as heroine, oxycodone and hydrocodone that are produced by modifying natural opium alkaloids (opiates) and have similar chemical structures; and pure synthetics such as fentanyl and methadone that are not produced from opium and may have very different chemical structures than the opium alkaloids. Additional examples of opioids are hydromorphone, oxymorphone, levorphanol, dihydrocodeine, meperidine, diphenoxylate, sufentanil, alfentanil, propoxyphene, pentazocine, nalbuphine, butorphanol, buprenorphine, meptazinol, dezocine, and pharmaceutically acceptable salts thereof.

The use of "hydrocodone" is meant to include a semisynthetic narcotic analgesic and antitussive prepared from codeine with multiple actions qualitatively similar to those of codeine. It is commonly used for the relief of moderate to moderately severe pain. Trade names include Anexsia™, Hycodan™, Hycomine™, Lorcet™, Lortab™, Norco™, Tussionex™, Tylox™, and Vicodin™. Other salt forms of hydrocodone, such as hydrocodone bitartrate and hydrocodone polistirex, are encompassed by the present technology.

Some embodiments of the present technology provide carboxylic acids conjugated to hydrocodone, where the carboxylic acid group is separated by an alkyl or alkenyl chain from the aromatic ring. The chain length of the alkyl or alkenyl group in some embodiments of the present technology do not exceed two unbranched carbon atoms, for example, 2 or 1, but is not limited in numbers of atoms on potential side-chains or additional functional groups. One embodiment of the present technology includes both carbon-only aryl, and aryl groups with heteroatoms (heteroaryl).

In some embodiments of the present technology, the aryl or heteroaryl group, which is connected through an alkyl or alkenyl chain to the carboxyl function, can be a 6-membered ring and contain zero or one heteroatom. In some embodiments, additional substituted or unsubstituted aromatic or aliphatic rings may be fused to this 6-membered aryl or heteroaryl moiety. In some embodiments of the present technology, the aryl carboxylic acids can have only one free carboxylic acid group and the total number of phenyl substituents on the 6-membered ring can be four or less, for example 4, 3, 2 or 1.

Some embodiments of the present technology provide at least one conjugate of hydrocodone and at least one phenylethanoic acid, phenylpropanoic acid, phenylpropenoic acid, a salt thereof, a derivative thereof or a combination thereof.

In some embodiments of the present technology at least one phenylethanoic acid, a salt thereof, a derivative thereof or a combination thereof is of formula I:

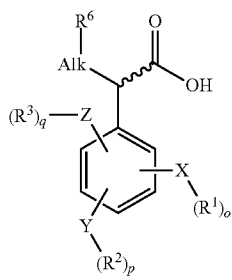

(I)

wherein,

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

Alk is an alkyl chain —$(CH_2)_n$— wherein n is 0 or 1; and $R^6$ is H, OH or carbonyl.

Suitable phenylethanoic acids and derivatives include phenylacetic acids, including various subsets of natural products, metabolites and pharmaceuticals. One such pharmaceutical subset includes, for example, "profens", a type of NSAIDs and derivatives of certain phenylpropionic acids (i.e., 2-methyl-2-phenylacetic acid analogs). Other suitable phenylethanoic acids and derivatives have central functions in the phenylalanine and tyrosine metabolism. Suitable phenylethanoic acids and derivatives can be found in FIG. 1 and include, but are not limited to, phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, D,L-tropic acid, diclofenac, D,L-mandelic acid, 3,4-dihydroxy-D,L-mandelic acid, vanillyl-D,L-mandelic acid, isovanillyl-D,L-mandelic acid, ibuprofen, fenoprofen, carprofen, flurbiprofen, ketoprofen, and naproxen.

In other embodiments of the present technology, at least one phenylpropenoic acid, phenylpropanoic acid, a salt thereof, a derivative thereof or a combination thereof is of formula II or formula III:

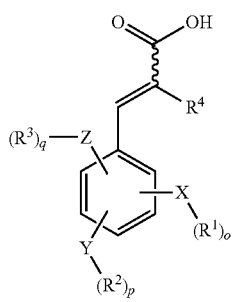

(II)

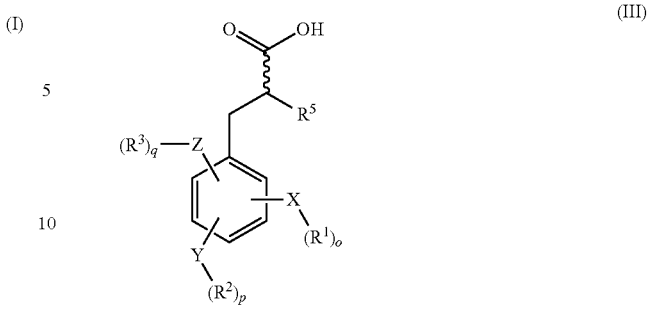

(III)

wherein,

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

$R^4$ is H or OH; and $R^5$ is H, OH or carbonyl.

Figure 2:
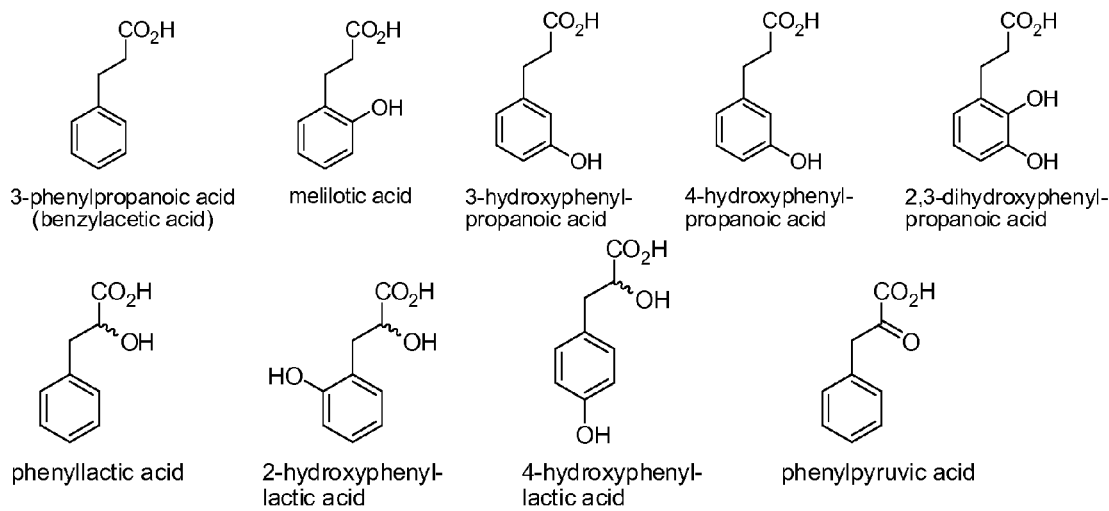
FIG. 2. Structures of some phenylpropanoic acids and derivatives for use in making the conjugates of the present technology.

Suitable phenylpropanoic acids and derivatives are defined by two carbons between the carboxyl function and the phenyl ring. Both the alkyl chain and the aryl moiety can have substituents, preferably hydroxyl groups. Some phenylpropanoic acid and derivatives of this class can be found in the phenylalanine metabolism. Suitable examples of phenylpropanoic acids and derivatives are found in FIG. 2 and include, but are not limited to, benzylacetic acid, melilotic acid, 3-hydroxyphenylpropanoic acid, 4-hydroxyphenylpropanoic acid, 2,3-dihydroxyphenylpropanoic acid, D,L-phenyllactic acid, o,m,p-hydroxy-D,L-phenyllactic acid, and phenylpyruvic acid.

Figure 3:
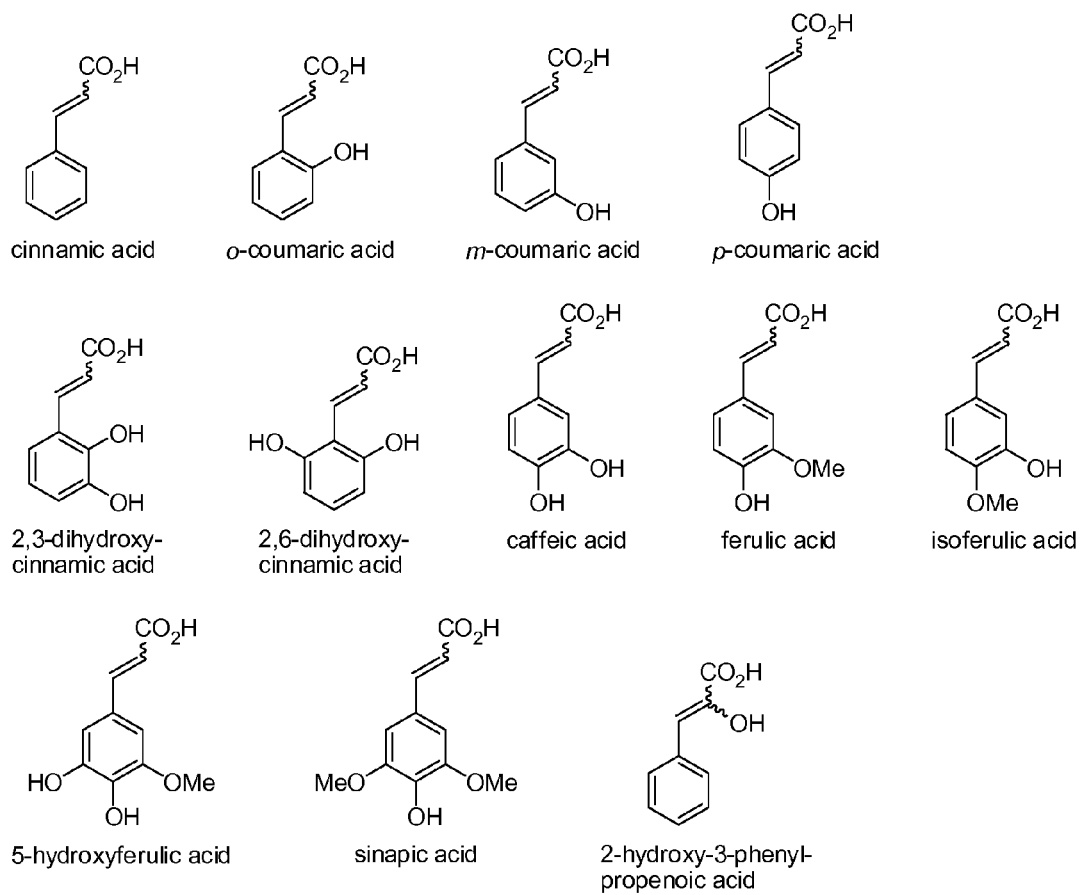
FIG. 3. Structures of some phenylpropenoic acids and derivatives for use in making the conjugates of the present technology.

Suitable phenylpropenoic acids and derivatives include cinnamic acids (3-phenylacrylic acids) which are unsaturated analogs of benzylacetic acids. Suitable phenylpropenoic acids and derivatives occur in two isomeric forms: cis (Z) and trans (E). In some embodiments, the isomers of the present technology are not limited to but are preferably in the trans configuration. Similar to phenylpropanoic acids, derivatives of cinnamic acid can be substituted on the alkenyl or aryl moiety of the molecule. In some embodiments, the substituents include, but are not limited to, hydroxyl and methoxy groups. Suitable phenylpropenoic acids and derivatives can be found in FIG. 3 and include, but are not limited to, cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, and 2-hydroxy-3-phenylpropenoic acid.

In another embodiment, the prodrug or hydrocodone conjugate of the present technology is ibuprofen-hydrocodone (Ibu-HC), which has the following structure:

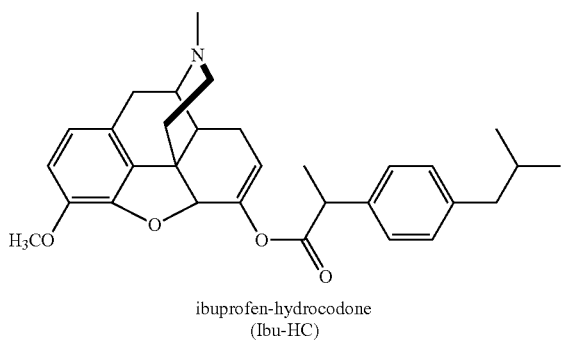

ibuprofen-hydrocodone
(Ibu-HC)

In another embodiment, the prodrug or hydrocodone conjugate of the present technology is cinnamate-hydrocodone (HC), which has the following structure:

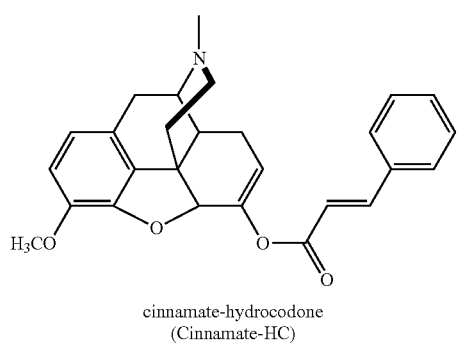

cinnamate-hydrocodone
(Cinnamate-HC)

In yet another embodiment, the prodrug or conjugate composition of the present technology is naproxen-hydrocodone (HC), which has the following structure:

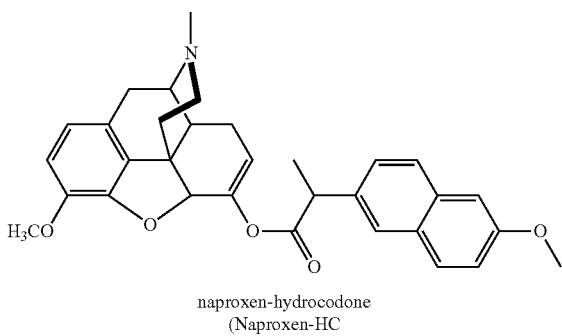

naproxen-hydrocodone
(Naproxen-HC

Some embodiments of the present technology provide a conjugate of hydrocodone that is broken down in vivo either enzymatically or otherwise, releasing the active hydrocodone and the respective aryl carboxylic acid or metabolites thereof. The aryl carboxylic acids used in the conjugates of the present technology are non-toxic at the given dosing levels and are preferably known drugs, natural products, metabolites, or GRAS (Generally Regarded As Safe) compounds (e.g., preservatives, dyes, flavors, etc.) or non-toxic mimetics thereof.

Compounds, compositions and methods of the present technology provide reduced potential for overdose, reduced potential for abuse or addiction and/or improve hydrocodone's characteristics with regard to high toxicities or suboptimal release profiles. Without wishing to be limited to the below theory, it is believed that overdose protection may occur due to the conjugates being exposed to different enzymes and/or metabolic pathways by oral administration where the conjugate is exposed through the gut and first-pass metabolism as opposed to the exposure to enzymes in the circulation or mucosal membranes which limits the ability of hydrocodone to be released from the conjugate. Therefore, abuse resistance is provided by limiting the "rush" or "high" available from the active hydrocodone released by the prodrug and limiting the effectiveness of alternative routes of administration.

The compositions of the present technology preferably have no or a substantially decreased pharmacological activity when administered through injection or intranasal routes of administration. However, they remain orally bioavailable. Again, not wanting to be bound by any particular theory, the bioavailability can be a result of the hydrolysis of the chemical linkage (i.e., a covalent linkage) following oral administration. In at least one embodiment, release of hydrocodone is reduced when the composition of the present technology is delivered by parenteral routes.

For example, in one embodiment, the composition of the present technology maintains its effectiveness and abuse resistance following the crushing of the tablet, capsule or other oral dosage form. In contrast, in use of nonconjugated (or "unconjugated") forms of hydrocodone, the hydrocodone is released immediately following crushing allowing the content of the crushed tablet to be used by injection or snorting producing the "rush" effect sought by addicts.

In some embodiments of the present technology, the conjugates of hydrocodone can be given orally to an animal or human patient, and, upon administration, release the active hydrocodone by being hydrolyzed in the body. Not to be bound by any particular theory, it is believed that since the aryl carboxylic acids are naturally occurring metabolites or mimetics thereof or pharmaceutically active compounds, these conjugates can be easily recognized by physiological systems resulting in hydrolysis and release of hydrocodone. The conjugates themselves have either no or limited pharmacological activity as a conjugate and consequently may follow a metabolic pathway that differs from the unconjugated drug.

In some embodiments of the present technology, the choice of suitable aryl carboxylic acids ("ligands") to conjugate to hydrocodone determines the release of hydrocodone into the systemic circulation and can be controlled even when the conjugate is administered via routes other than oral. In one embodiment, the modified hydrocodone would release hydrocodone similar to unconjugated or unmodified hydrocodone. In another embodiment, the conjugated hydrocodone releases hydrocodone in a controlled or sustained release profile. In some embodiments, this controlled release can alleviate certain side-effects and improve upon the safety profile of the unconjugated drug. These side-effects may include, but are not limited to, anxiety, bruising, constipation, decreased appetite, difficulty breathing, dizziness, drowsiness, dry throat, diarrhea, headache, nausea, stomach cramps, stomach pain, or vomiting. In another embodiment, the conjugated hydrocodone would selectively allow hydrocodone to be metabolized to hydromorphone. In some embodiments, these conjugates can be used for pain relief, such as moderate to severe pain relief.

Hydrocodone and other opioids are also highly addictive and prone to substance abuse. Recreational drug abuse of opioids is a common problem and usually begins with oral doses taken with the purpose of achieving euphoria ("rush", "high"). Over time the drug abuser often increases the oral dosages to attain more powerful "highs" or to compensate for heightened opioid tolerance. This behavior can escalate and result in exploring of other routes of administration such as intranasal ("snorting") and intravenous ("shooting").

In some embodiments of the present technology, the hydrocodone that is conjugated with a suitable aryl carboxylic acid ligand does not result in rapid spikes in plasma concentrations after oral administration that is sought by a potential drug abuser. In some embodiments, hydrocodone released from these conjugates has a delayed $T_{max}$ and possibly lower $C_{max}$ than the unconjugated drug. Not to be bound by any particular theory, it is believed that the conjugates of the present technology when taken orally or by other non-oral routes do not provide the feeling of a "rush" even when taken at higher doses but still maintain pain relief.

Additionally, in some embodiments, hydrocodone conjugated with appropriate ligands of the present technology is not hydrolyzed efficiently when administered via non-oral routes. As a result, these conjugates do not generate high plasma or blood concentrations of released hydrocodone when injected or snorted compared to free hydrocodone administered through these routes, which may be seen by a lower $C_{max}$ and/or a reduced AUC.

In some embodiments, the conjugates of the present technology, since they consist of covalently bound hydrocodone, are not able to be physically manipulated to release the hydrocodone opioid from the conjugated hydrocodone by methods, for example, of grinding up or crushing of solid forms. Further, the conjugates of the present technology provide resistance to chemical hydrolysis under conditions a potential drug abuser may apply to "extract" the active portion of the molecule, for example, by boiling, or acidic or basic solution treatment of the conjugate.

The compositions or prodrugs of the present technology can be oral dosage forms. These dosage forms include but are not limited to tablet, capsule, caplet, troche, lozenge, powder, suspension, syrup, solution or oral thin film (OTF). Preferred oral administration forms are capsule, tablet, solutions and OTF.

Solid dosage forms can include, but are not limited to, the following types of excipients: antiadherents, binders, coatings, disintegrants, fillers, flavors and colors, glidants, lubricants, preservatives, sorbents and sweeteners.

Oral formulations of the present technology can also be included in a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which is then placed in the feeding tube of a patient who is unable to swallow.

Soft gel or soft gelatin capsules may be prepared, for example by dispersing the formulation in an appropriate vehicle (vegetable oils are commonly used) to form a high viscosity mixture. This mixture is then encapsulated with a gelatin based film using technology and machinery known to those in the soft gel industry. The individual units so formed are then dried to constant weight.

Chewable tablets, for example, may be prepared by mixing the formulations with excipients designed to form a relatively soft, flavored, tablet dosage form that is intended to be chewed rather than swallowed. Conventional tablet machinery and procedures, for example, direct compression and granulation, i.e., or slugging, before compression, can be utilized. Those individuals involved in pharmaceutical solid dosage form production are versed in the processes and the machinery used as the chewable dosage form is a very common dosage form in the pharmaceutical industry.

Film coated tablets, for example may be prepared by coating tablets using techniques such as rotating pan coating methods or air suspension methods to deposit a contiguous film layer on a tablet.

Compressed tablets, for example may be prepared by mixing the formulation with excipients intended to add binding qualities to disintegration qualities. The mixture is either directly compressed or granulated then compressed using methods and machinery known to those in the industry. The resultant compressed tablet dosage units are then packaged according to market choice, such as in unit dose, rolls, bulk bottles, blister packs, etc.

The present technology also contemplates the use of biologically-acceptable carriers which may be prepared from a wide range of materials. Without being limited, such materials include diluents, binders and adhesives, lubricants, plasticizers, disintegrants, colorants, bulking substances, flavorings, sweeteners and miscellaneous materials such as buffers and adsorbents in order to prepare a particular medicated composition.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons working in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

It should be understood that in addition to the ingredients particularly mentioned above, the formulations of the present technology can include other suitable agents such as flavoring agents, preservatives and antioxidants. Such antioxidants would be food acceptable and could include vitamin E, carotene, BHT or other antioxidants.

Other compounds which may be included by admixture are, for example, medically inert ingredients, e.g. solid and liquid diluent, such as lactose, dextrose, saccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulfates; and other therapeutically acceptable accessory ingredients, such as humectants, preservatives, buffers and antioxidants, which are known additives for such formulations.

For oral administration, fine powders or granules containing diluting, dispersing and/or surface-active agents may be presented in a draught, in water or a syrup, in capsules or sachets in the dry state, in a non-aqueous suspension wherein suspending agents may be included, or in a suspension in water or a syrup. Where desirable, flavoring, preserving, suspending, thickening or emulsifying agents can be included.

Liquid dispersions for oral administration may be syrups, emulsions or suspensions. The syrups may contain as carrier, for example, saccharose or saccharose with glycerol and/or mannitol and/or sorbitol. In particular a syrup for diabetic patients can contain as carriers only products, for example sorbitol, which do not metabolize to glucose or which metabolize only a very small amount to glucose. The suspensions and the emulsions may contain a carrier, for example a natural gum, agar, sodium alginate, pectin, methylcellulose, carboxymethylcellulose or polyvinyl alcohol.

Current approved formulations of hydrocodone are combination therapies of hydrocodone and one or more other non-narcotic active ingredient depending on intended indication. Examples of these active pharmaceuticals include, but are not limited to, acetaminophen, phenylpropanolamine, homatropine, ibuprofen, aspirin, pheniramine, chlorpheniramine, phenylephrine, pseudoephedrine, pyrilamine and guaifenesin. The conjugated hydrocodone of the present technology can be formulated with one or a combination of these or other active substances or as standalone active ingredient without any other actives.

The conjugate compositions or prodrugs may be used in methods of treating a patient having a disease, disorder or condition requiring binding or inhibiting binding of an opioid to the opioid receptors of the patient. Treatment comprises orally administering to the patient a pharmaceutically effective amount of at least one conjugate of hydrocodone as described in the present technology. The conjugate can exhibit an improved rate of release over time, for example a slower release over time and a pharmacologically effective AUC when compared to a molar equivalent amount of unconjugated hydrocodone. In other embodiments, at least one conjugate can provide less variability in the oral PK profile when compared to a molar equivalent amount of unconjugated hydrocodone.

In other embodiments, at least one conjugate is provided in an amount sufficient to provide a therapeutically bioequivalent AUC (area under the curve) when compared to unconjugated hydrocodone. In further embodiments, the conjugate is provided in an amount sufficient to provide a therapeutically bioequivalent AUC when compared to hydrocodone alone but does not provide a $C_{max}$ spike in plasma or does not provide an equivalent $C_{max}$ in plasma concentrations. In some aspects, the conjugate is provided in an amount sufficient to provide a therapeutically equivalent Cmax when compared to unconjugated hydrocodone.

Suitable diseases, disorders or conditions that can be treated by the prodrugs or compositions of the present technology include narcotic addiction or drug addiction and/or acute or chronic pain.

Dosages for the conjugates of the present technology depend on their molecular weight and the respective weight-percentage of hydrocodone as part of the whole conjugate, and therefore can be higher than the dosages of free hydrocodone. Dosages can be calculated based on the strengths of dosages of hydrocodone bitartrate which range between 2.5 mg and 15 mg per dose. Dose conversion from hydrocodone bitartrate to hydrocodone prodrug can be performed using the following formula:

dose(HC prodrug/conjugate)=[dose(HC bitartrate)× (molecular weight(HC prodrug/conjugate)/ 494.49)]/proportion of hydrocodone released from prodrug/conjugate HC: hydrocodone Suitable dosages of the conjugated hydrocodone of the present technology include, but are not limited to, formulations including from about 0.5 mg or higher, alternatively from about 2.5 mg or higher, alternatively from about 5.0 mg or higher, alternatively from about 7.5 mg or higher, alternatively from about 10 mg or higher, alternatively from about 20 mg or higher, alternatively from about 30 mg or higher, alternatively from about 40 mg or higher, alternatively from about 50 mg or higher, alternatively from about 60 mg or higher, alternatively from about 70 mg or higher, alternatively from about 80 mg or higher, alternatively from about 90 mg or higher, alternatively from about 100 mg or higher, and include any additional increments thereof, for example, 0.1, 0.2, 0.25, 0.3, 0.4, 0.5, 0.6, 0.7, 0.75, 0.8, 0.9 or 1.0 mg and multiplied factors thereof, (e.g. ×1, ×2, ×2.5, ×5, ×10, ×100, etc). The present technology also includes dosage formulations including currently approved formulations of hydrocodone (See FIG. 4), where the dosage can be calculated using the above-noted formula determined by the amount of hydrocodone-bitartrate. The present technology provides for dosage forms formulated as a single therapy or as a combination therapy with other API's (FIG. 4).

The conjugates of hydrocodone of the present technology have a number of advantages including, but not limited to, a reduced patient variability of plasma concentrations of hydrocodone or hydromorphone when compared to free hydrocodone, reduced drug abuse potential, reduced risk of chemical or physical manipulation resulting in full dosage of hydrocodone released, improved dosage forms through covalent linkage to carboxylic acids or derivatives thereof, increased or decreased metabolism of hydrocodone to hydromorphone and/or decreased side-effects other than drug abuse.

In another embodiment, hydrocodone conjugates or prodrugs of the present technology can produce hydrocodone and hydromorphone plasma concentrations that are significantly lower than respective plasma concentration for unconjugated Hydrocodone•BT or for other prodrug classes when administered intranasally.

Hydrocodone is a narcotic analgesic, which acts as a weak agonist at opioid receptors in the central nervous system (CNS). It primarily affects the μ (mu) receptor (OP3), but also exhibits agonist activity at the δ (delta) receptor (OP1) and κ (kappa) receptor (OP2). Additionally, hydrocodone displays antitussive properties by suppressing the cough reflex in the medullary cough center of the brain.

Side effects of opioid analgesics include gastrointestinal dysfunction caused by the opioids binding to the mu (μ) receptors present in the gastrointestinal tract. The side-effects in the stomach include a reduction in the secretion of hydrochloric acid, decreased gastric motility, thus prolonging gastric emptying time, which can result in esophageal reflux. Passage of the gastric contents through the duodenum may be delayed by as much as 12 hours, and the absorption of orally administered drugs is retarded. In the small intestines the opioid analgesics diminish biliary, pancreatic and intestinal secretions and delay digestion of food in the small intestine. Propulsive peristaltic waves in the colon are diminished or abolished after administration of opioids, and tone is increased to the point of spasm. The resulting delay in the passage of bowel contents causes considerable desiccation of the feces, which, in turn retards their advance through the colon. These actions, combined with inattention to the normal sensory stimuli for defecation reflex due to the central actions of the drug, contribute to opioid-induced constipation.

Hydrocodone is used for the treatment of moderate to moderately severe pain and for inhibition of cough (especially dry, nonproductive cough). The prodrugs of the present technology may be administered for the relief of pain or for cough depression or for the treatment of any condition that may require the blocking of opioid receptors.

The conjugates of the present technology can provide a decrease in side effects of the opioid analgesic, including reduced or inhibited constipatory effects.

The present technology also provides a method of synthesis for the preparation of the conjugated hydrocodone of the present technology. In one embodiment, the synthesis of the present technology includes the steps of:
1. Protection of the ligand, if necessary;
2. Activation of the ligand carboxylic acid group, if not already in activated form;
3. Addition of the activated ligand to hydrocodone or vice versa in the presence of base; and
4. Removal of ligand protecting groups, if applicable.

If the aryl carboxylic acid contains any additional reactive functional groups that may interfere with the coupling to hydrocodone, it may be necessary to first attach one or more protecting groups. Any suitable protecting group may be used depending on the type of functional group and reaction conditions. Some protecting group examples are: acetyl (Ac), β-methoxyethoxymethyl ether (MEM), methoxymethyl ether (MOM), p-methoxybenzyl ether (PMB), trimethylsilyl (TMS), tert.-butyldimethylsilyl (TBDPS), triisopropylsilyl (TIPS), carbobenzyloxy (Cbz), p-methoxybenzyl carbonyl (Moz), tert.-butyloxycarbonyl (Boc), 9-fluorenylmethyloxycarbonyl (Fmoc), benzyl (Bn), p-methoxybenzyl (MPM), and tosyl (Ts). Temporary formation of acetals or ketals from carbonyl functions may also be appropriate.

The carboxylic acid group of the ligands should be activated in order to react with hydrocodone and to generate appreciable amounts of conjugate. This activation can be accomplished in numerous ways by a variety of coupling agents. Examples of such coupling agents are: N,N'-dicyclohexylcarbodiimide (DCC), N-(3-dimethylaminopropyl)-N'-ethylcarbodiimide (EDCI), N,N'-diisopropylcarbodiimide (DIC), 1,1'-carbonyldiimidazole (CDI) or other carbodiimides; (benzotriazol-1-yloxy)tris(dimethylamino)phosphonium hexafluorophosphate (BOP), bromotripyrrolidinophosphonium hexafluorophosphate (PyBroP), (benzotriazol-1-yloxy)tripyrrolidinophosphonium hexafluorophosphate (PyBOP) or other phosphonium-based reagents; O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), fluoro-N,N,N',N'-tetramethylformamidinium hexafluorophosphate (TFFH), N,N,N',N'-tetramethyl-O-(N-succinimidyl)uronium tetrafluoroborate (TSTU) or other aminium-based reagents. The aryl carboxylic acid can also be converted to a suitable acyl halide, acyl azide or mixed anhydride.

A base may be required at any step in the synthetic scheme of an aryl carboxylic acid conjugate of hydrocodone. Suitable bases include but are not limited to: 4-methylmorpholine (NMM), 4-(dimethylamino)pyridine (DMAP), N,N-diisopropylethylamine, lithium bis(trimethylsilyl)amide, lithium diisopropylamide (LDA), any alkali metal tert.-butoxide (e.g., potassium tert.-butoxide), any alkali metal hydride (e.g., sodium hydride), any alkali metal alkoxide (e.g., sodium methoxide), triethylamine or any other tertiary amine.

Suitable solvents that can be used for any reaction in the synthetic scheme of an aryl carboxylic acid conjugate of hydrocodone include but are not limited to: acetone, acetonitrile, butanol, chloroform, dichloromethane, dimethylformamide (DMF), dimethylsulfoxide (DMSO), dioxane, ethanol, ethyl acetate, diethyl ether, heptane, hexane, methanol, methyl tert.-butyl ether (MTBE), isopropanol, isopropyl acetate, diisopropyl ether, tetrahydrofuran, toluene, xylene or water.

The present technology provides pharmaceutical kits for the treatment or prevention of drug withdrawal symptoms or pain in a patient. The patient may be a human or animal patient. Suitable human patients include pediatric patients, geriatric (elderly) patients, and normative patients. The kit comprises a specific amount of the individual doses in a package containing a pharmaceutically effective amount of at least one conjugate of hydrocodone of the present technology. The kit can further include instructions for use of the kit. The specified amount of individual doses may contain from about 1 to about 100 individual dosages, alternatively from about 1 to about 60 individual dosages, alternatively from about 10 to about 30 individual dosages, including, about 1, about 2, about 5, about 10, about 15, about 20, about 25, about 30, about 35, about 40, about 45, about 50, about 55, about 60, about 70, about 80, about 100, and include any additional increments thereof, for example, 1, 2, 5, 10 and multiplied factors thereof, (e.g. ×1, ×2, ×2.5, ×5, ×10, ×100, etc).

In one embodiment of the present technology provides cinnamate-HC, which could not be dosed to rats intranasally due to hydrophobic nature and inability to be solubilized in water. Not to be bound by any particular theory, it can be assumed that this compound would also congeal or become clumpy when a human subject tries to inhale it intranasally ("snorting"). This property would not only make an attempt of intranasal abuse an unpleasant experience but would likely also prevent the prodrug from permeating the nose mucosa. As a consequence, this compound becomes ineffective for this route of administration.

The presently described technology and its advantages will be better understood by reference to the following examples. These examples are provided to describe specific embodiments of the present technology. By providing these specific examples, it is not intended to limit the scope and spirit of the present technology. It will be understood by those skilled in the art that the full scope of the presently described technology encompasses the subject matter defined by the claims appending this specification, and any alterations, modifications, or equivalents of those claims.

EXAMPLES

Example 1

Chemical Stability of Conjugates of Hydrocodone

Exemplary conjugates of hydrocodone of the present technology and control test conjugates not of the present technology (Adipate-HC or Tyr-Tyr-Phe-Phe-Ile-hydrocodone [YY-FFI-HC]) were tested for chemical stability under conditions similar to what a potential drug abused may use to "extract" the active portion of the molecule, for example dissolved in hydrochloric acid or sodium bicarbonate either at ambient temperature or at 100° C.

Samples of conjugates of hydrocodone of the present technology were tested and compared with samples of other conjugates not of the present technology for their hydrolysis to hydrocodone after dilution in 1 N hydrochloric acid (HCl) for 1 hour at ambient temperature (~20° C.) or in an oil bath at 100° C. The percentages indicate how much of the initial amount of conjugate was hydrolyzed under these conditions.

The results are shown in Table 1.

TABLE 1

| | 1 N HCl | |
|---|---|---|
| Compound | ambient | 100° C. |
| Naproxen-HC | 0% | 33% |
| Adipate-HC | 13% | 100% |

Samples of each conjugate were dissolved in a solution of 5% NaHCO3 for one hour at either ambient temperature (~20° C.) or in an oil bath at 100° C. The percentages indicate how much of the initial amount of conjugate was hydrolyzed under these conditions as shown in Table 2.

TABLE 2

| | 5% NaHCO$_3$ | |
|---|---|---|
| Compound | ambient | 100° C. |
| Naproxen-HC | 0% | 8% |
| Ibu-HC | 0% | 22% |
| YYFFI-HC | 0% | 70% |
| Adipate-HC | 3% | 100% |

Example 2

Oral PK Profiles of Conjugated Hydrocodone of the Present Technology

The PK profiles for hydrocodone or hydromorphone released from the prodrugs of the present technology can be selected to control and modulate release to resemble various desirable curve shapes (depending on application) while maintaining beneficial chemical, intranasal and intravenous abuse resistance.

Figure 5:
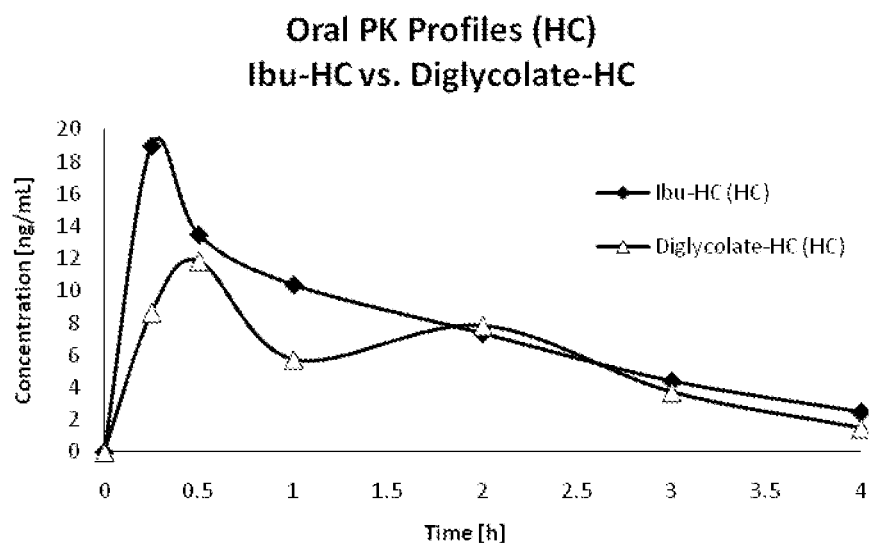
FIG. 5. Plasma concentrations of hydrocodone released from Ibu-HC and Diglycolate-HC over time upon oral administration in rats.
Figure 6:
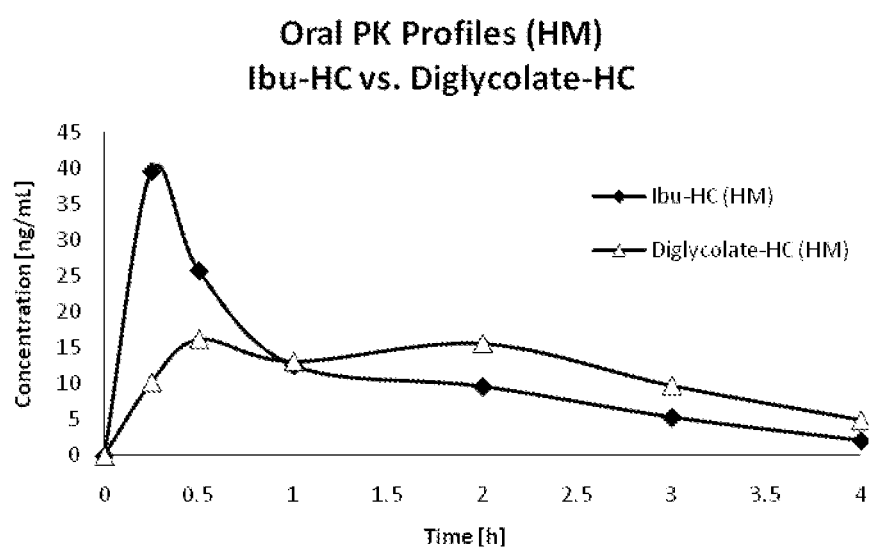
FIG. 6. Plasma concentrations of active metabolite hydromorphone over time upon oral administration of Ibu-HC and Diglycolate-HC in rats.

Comparison was performed for Ibu-HC, an exemplary prodrug of the current technology with Diglycolate-HC, a conjugate not within the scope of the present technology. Rats were orally administered the equivalent of 2 mg/kg of hydrocodone freebase of the conjugate and the plasma concentrations of released hydrocodone and of the active metabolite hydromorphone were measured over time by LC-MS/MS. Hydrocodone plasma concentrations produced by Ibu-HC were higher during the initial 1-2 hours than hydrocodone concentrations generated by Diglycolate-HC (AUC and $C_{max}$ for Ibu-HC were approximately 30% and 60% higher, respectively) (See FIG. 5). Moreover, Ibu-HC generated higher plasma concentrations of the much more potent active metabolite hydromorphone during the crucial first hour (for immediate pain relief) than Diglycolate-HC (See FIG. 6; AUC values were similar, but $C_{max}$ for Ibu-HC was approximately 155% higher). This suggests that both compounds undergo a different metabolic pathway and potentially a greater pain relieving effect. Thus, some embodiments of the present conjugates provide a high initial plasma level of hydrocodone and/or hydromorphone, which may be desired for some treatments.

Example 3

Exemplary Intranasal PK Profiles of Hydrocodone Conjugates of the Present Technology By selecting suitable phenylethanoic, phenylpropanoic or phenylpropenoic acid analogs the resulting hydrocodone prodrugs are not hydrolyzed efficiently when administered via routes other than oral. Prodrugs of the present technology with appropriately elected ligands can produce hydrocodone and hydromorphone plasma concentrations that are significantly lower than respective plasma concentration for unbound Hydrocodone•BT or for other prodrug classes when administered intranasally.

Figure 7:
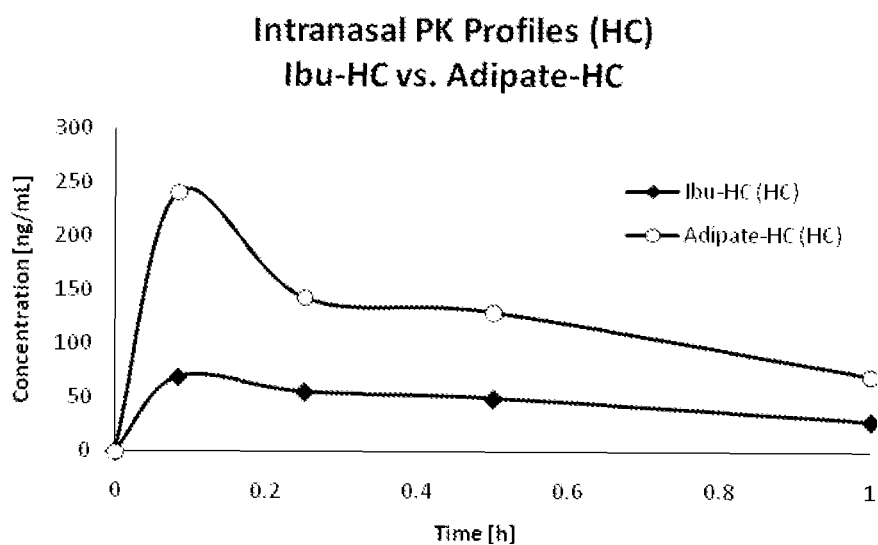
FIG. 7. Plasma concentrations of hydrocodone released from Ibu-HC and Adipate-HC over time upon intranasal administration in rats.
Figure 8:
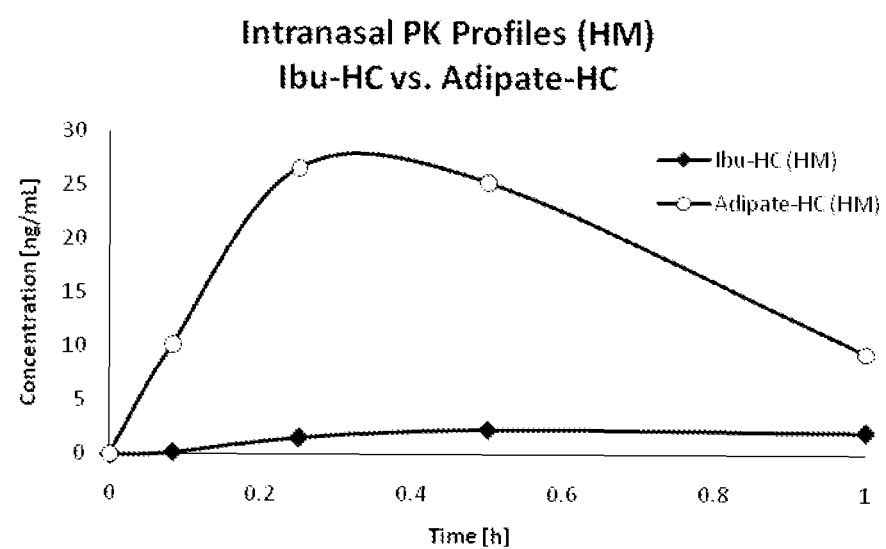
FIG. 8. Plasma concentrations of active metabolite hydromorphone over time upon intranasal administration of Ibu-HC and Adipate-HC in rats.

Ibu-HC and Adipate-HC were administered to rats intranasally at doses equivalent to 2 mg/kg of freebase hydrocodone and the plasma concentrations of released hydrocodone and of the active metabolite hydromorphone were measured by LC-MS/MS over time. Ibu-HC exhibited better abuse protection than Adipate-HC since hydrocodone plasma concentrations were significantly lower for Ibu-HC (FIG. 7; AUC and $C_{max}$ for Adipate-HC were approximately 170% and 245% higher, respectively). Moreover, Ibu-HC produced a very low plasma concentration of hydromorphone when compared to Adipate-HC (FIG. 8; AUC and $C_{max}$ for Adipate-HC were approximately 940% and 1,010% higher, respectively).

Example 4

Exemplary Intravenous PK Profiles of Hydrocodone Conjugates of the Present Technology Some of the phenylethanoic, phenylpropanoic or phenylpropenoic acid hydrocodone conjugates or prodrugs are hydrophobic and thus poorly water-soluble. Some hydrophobic prodrugs of the present technology have very low water solubility, and include, but are not limited to, Ibu-HC and Cinnamate-HC. Ibu-HC and Cinnamate-HC cannot be administered intravenously at oral equivalent doses because they cannot dissolve in a practical amount of water (injectable compounds must be completely in solution, because any solid particle may cause an embolism). The amount of water necessary to dissolve a desirable amount of conjugate would make an injection unfeasible and thus make these compounds drug-abuse resistance by injection. This is in contrast to other classes of prodrugs not encompassed in the present technology that are water-soluble and could be dosed intravenously in rats at oral equivalent doses, including Adipate-HC and Diglycolate-HC.

Example 5

Comparison of Oral PK Profiles of Hydrocodone Conjugates

Figure 9:
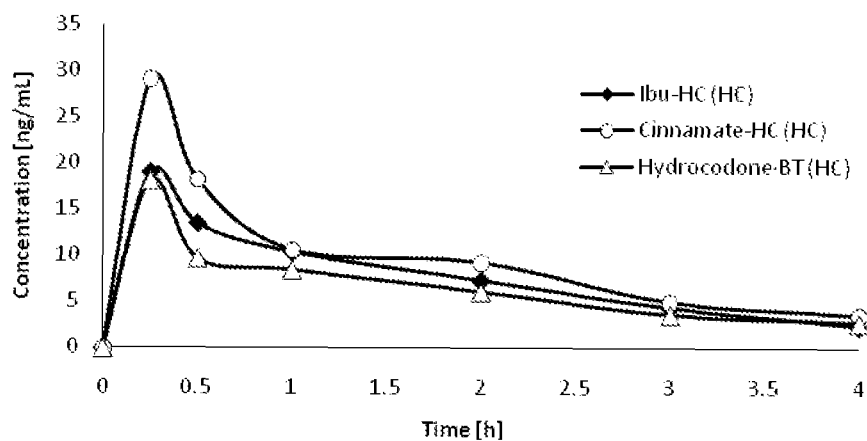
FIG. 9. Plasma concentrations of hydrocodone released from Ibu-HC, Cinnamate-HC and Hydrocodone•BT over time upon oral administration in rats.
Figure 10:
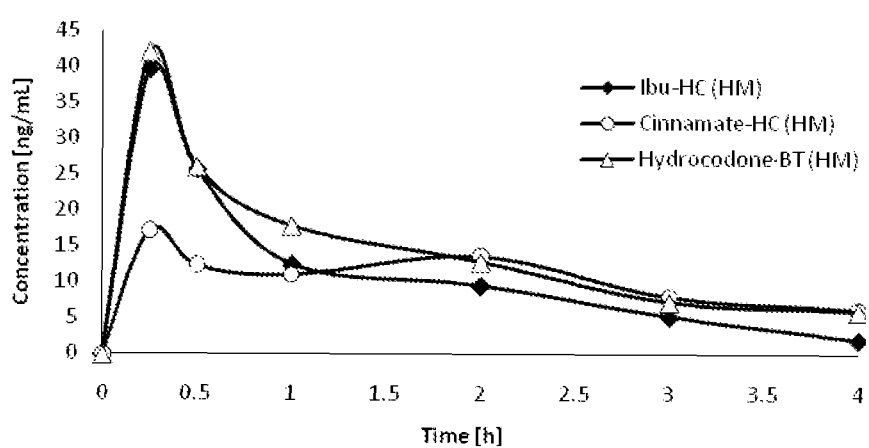
FIG. 10. Plasma concentrations of active metabolite hydromorphone over time upon oral administration of Ibu-HC, Cinnamate-HC and Hydrocodone•BT in rats.

Oral PK profiles of hydrocodone conjugates were tested by administering Ibu-HC, cinnamate-HC or unconjugated Hydrocodone BT to rats at doses equivalent to 2 mg/kg of freebase hydrocodone and measuring the plasma concentrations of released hydrocodone or of active metabolite hydromorphone over time. After oral administration, Ibu-HC produced hydrocodone and hydromorphone plasma concentrations that were similar to the respective concentrations found for unconjugated Hydrocodone•BT (FIG. 9 and FIG. 10). The corresponding AUC and $C_{max}$ values were within the range of bioequivalence for the same dose (based on hydrocodone freebase).

During the first hour the oral PK profile of hydrocodone released from Cinnamate-HC exhibited a somewhat larger spike when compared to the parent drug, Hydrocodone•BT (FIG. 9). However, during subsequent elimination hydrocodone plasma concentrations were similar for both compounds. The opposite was found for the active metabolite, hydromorphone (FIG. 10). Unlike unbound Hydrocodone•BT, oral administration of Cinnamate-HC did not create a pronounced initial spike of hydromorphone plasma concentrations. The concentrations of the active metabolite produced by Cinnamate-HC remained within a relatively close range of the $C_{max}$ until the two hour time point. This resulted in a much flatter PK profile of hydromorphone for Cinnamate-HC when compared to Hydrocodone•BT.

Example 6

Intranasal PK Profiles of Hydrocodone Conjugates

Figure 11:
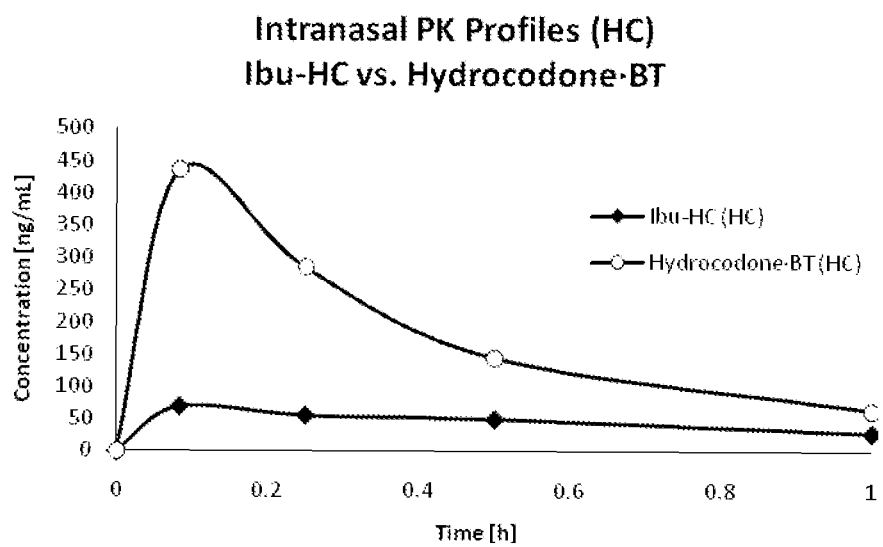
FIG. 11. Plasma concentrations of hydrocodone released from Ibu-HC and Hydrocodone•BT over time upon intranasal administration in rats.
Figure 12:
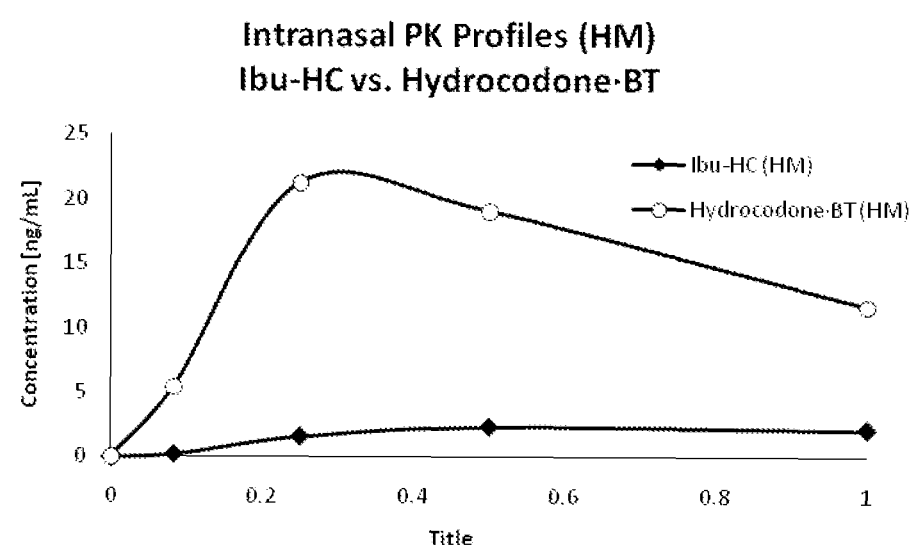
FIG. 12. Plasma concentrations of active metabolite hydromorphone over time upon intranasal administration of Ibu-HC and Hydrocodone•BT in rats.

The intranasal profiles of Ibu-HC were compared to the unconjugated drug Hydrocodone•BT by administering to rats intranasally and measuring the plasma concentration of hydrocodone or hydromorphone over time. Hydrocodone plasma concentrations were significantly lower for Ibu-HC (FIG. 11; AUC and $C_{max}$ for Hydrocodone•BT were approximately 300% and 525% higher, respectively). Moreover, Ibu-HC produced very low plasma concentration of hydromorphone when compared to Hydrocodone•BT (FIG. 12; AUC and $C_{max}$ for Hydrocodone•BT were approximately 745% and 790% higher, respectively).

Example 7

Synthesis of Conjugates of Hydrocodone

Synthesis of Cinnamic Acid Ester of Hydrocodone:
Cinnamoyl chloride (0.416 g, 2.5 mmol) was dissolved in a mixture of chloroform (10 mL) and pyridine (3 mL). Hydrocodone free base (0.45 g, 1.5 mmol) was added in small portions. The resulting solution was refluxed overnight while stirring. Solvents were evaporated to dryness. The resulting residue was dissolved in chloroform (150 mL), washed with aqueous sat. NaHCO$_3$ (60 mL×2) and 5% brine (60 mL×2). The organic layer was dried over anhydrous Na$_2$SO$_4$ and concentrated. The residue was purified by preparative TLC (10% methanol in dicloromethane) to give 0.42 g of a brownish amorphous solid. The yield was 65.1%. (See FIG. 13C)

Synthesis of Ibuprofen Ester of Hydrocodone:
To hydrocodone freebase (0.30 g, 1 mmol) in 15 mL of anhydrous THF was added a solution of LiHMDS in THF (1 M, 3 mL, 3 mmol) over 20 min. The mixture was stirred for 30 min. and ibuprofen succinate (0.91 g, 3 mmol) was added in one portion. The reaction was stirred for 6 hr. and subsequently quenched with 60 mL of sat. NH$_4$Cl. The mixture was stirred for 2 hr. and extracted with 150 mL of ethyl acetate. The ethyl acetate layer was washed with sat. NH$_4$Cl (3×60 mL) and water (60 mL), dried over anhydrous Na$_2$SO$_4$ and concentrated. The residue was purified by preparative TLC (7% methanol in dichloromethane). The product was dissolved in 100 mL of ethyl acetate and washed with sat. NaHCO$_3$ (5×40 mL) to remove most of the remaining unreacted ibuprofen. After drying and concentrating, 170 mg (35%) of a waxy solid was obtained.

In the present specification, use of the singular includes the plural except where specifically indicated.

The compositions, prodrugs, and methods described herein can be illustrated by the following embodiments enumerated in the numbered paragraphs that follow:

1. A composition comprising at least one conjugate of hydrocodone and at least one of phenylethanoic acid, phenylpropanoic acid, phenylpropenoic acid, a salt thereof, a derivative thereof or a combination thereof.

2. The composition of paragraph 1, wherein the conjugate comprises at least one phenylethanoic acid, a salt thereof, a derivative thereof or a combination thereof having the formula I:

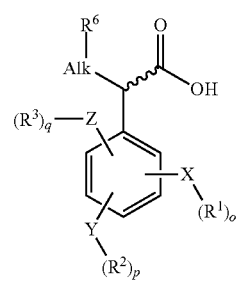

(I)

wherein,
X, Y and Z are independently selected from the group consisting of H, O, S, NH and —(CH$_2$)$_x$—;
R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;
o, p, q are independently selected from 0 or 1;
x is an integer between 1 and 10;
Alk is an alkyl chain —(CH$_2$)$_n$— wherein n is 0 or 1; and
R$^6$ is H, OH or carbonyl.

3. The composition of paragraph 2, wherein the phenylethanoic acid or derivative is a profen.

4. The composition of paragraph 2, wherein the phenylethanoic acid or derivative is a tyrosine metabolite.

5. The composition of paragraph 1, wherein the conjugate comprises at least one phenylpropenoic acid, phenylpropanoic acid, a salt thereof, a derivative thereof or a combination thereof having the formula II or formula III:

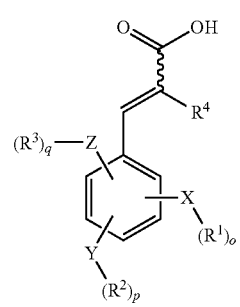

(II)

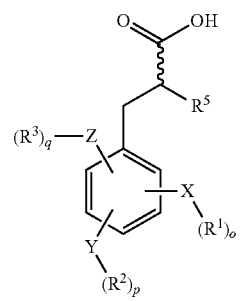

(III)

wherein,
X, Y and Z are independently selected from the group consisting of H, O, S, NH and —(CH$_2$)$_x$—;

R¹, R² and R³ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;
x is an integer between 1 and 10;
R⁴ is H or OH; and
R⁵ is H, OH or carbonyl.

6. The composition of paragraph 1, wherein the conjugate comprises at least one phenylethanoic acid or derivative selected from the group consisting of: phenylacetic acid (hydratropic acid), 2-hydroxyphenylacetic acid, 3-hydroxyphenylacetic acid, 4-hydroxyphenylacetic acid, homoprotocatechuic acid, homogentisic acid, 2,6-dihydroxyphenylacetic acid, homovanillic acid, homoisovanillic acid, homoveratric acid, atropic acid, D,L-tropic acid, diclofenac, D,L-mandelic acid, 3,4-dihydroxy-D,L-mandelic acid, vanillyl-D,L-mandelic acid, isovanillyl-D,L-mandelic acid, ibuprofen, fenoprofen, carprofen, flurbiprofen, ketoprofen, naproxen, derivatives thereof and combinations thereof.

7. The composition of paragraph 1, wherein the conjugate comprises at least one phenylpropanoic acid or derivative selected from the group consisting of: benzylacetic acid, melilotic acid, 3-hydroxyphenylpropanoic acid, 4-hydroxyphenylpropanoic acid, 2,3-dihydroxyphenylpropanoic acid, D,L-phenyllactic acid, o,m,p-hydroxy-D,L-phenyllactic acid, phenylpyruvic acid, derivatives thereof and combinations thereof.

8. The composition of paragraph 1, wherein the conjugate comprises at least one phenylpropenoic acid or derivative selected from a group consisting of: cinnamic acid, o,m,p-coumaric acid, 2,3-dihydroxycinnamic acid, 2,6-dihydroxycinnamic acid, caffeic acid, ferulic acid, isoferulic acid, 5-hydroxyferulic acid, sinapic acid, 2-hydroxy-3-phenylpropenoic acid, derivatives thereof and combinations thereof.

9. The composition of paragraph 1, wherein at least one conjugate is ibuprofen-hydrocodone.

10. The composition of paragraph 1, wherein at least one conjugate is cinnamate-hydrocodone.

11. The composition of paragraph 1, wherein at least one conjugate is naproxen-hydrocodone.

12. A composition comprising a phenylethanoate-hydrocodone conjugate, a phenylpropanoate-hydrocodone conjugate, a phenylpropenoate-hydrocodone conjugate, a salt thereof, a derivative thereof or a combination thereof.

13. The composition of paragraph 12, wherein the composition comprises a phenylethanoate-hydrocodone conjugate which is a conjugate of hydrocodone and at least one phenylethanoic acid, a salt thereof, a derivative thereof or a combination thereof having the formula I:

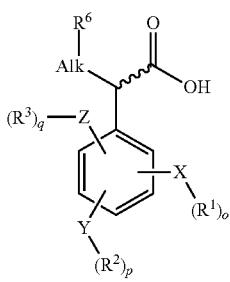

(I)

wherein,
X, Y and Z are independently selected from the group consisting of H, O, S, NH and —(CH₂)$_x$—;
R¹, R² and R³ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;
o, p, q are independently selected from 0 or 1;
x is an integer between 1 and 10;
Alk is an alkyl chain —(CH₂)$_n$— wherein n is 0 or 1; and
R⁶ is H, OH or carbonyl.

14. The composition of paragraph 12, wherein the composition comprises at least one phenylpropanoate-hydrocodone conjugate or phenylpropenoate-hydrocodone conjugate which is a conjugate of hydrocodone and at least one phenylpropenoic acid or phenylpropanoic acid, a salt thereof, a derivative thereof or a combination thereof of formula II or formula III:

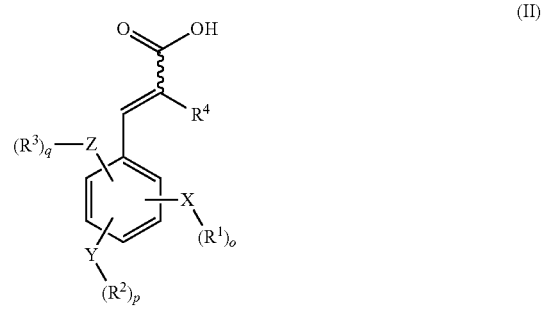

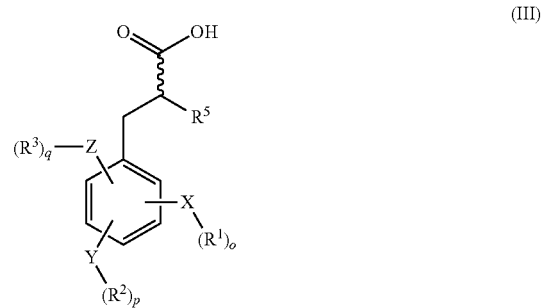

wherein,
X, Y and Z are independently selected from the group consisting of H, O, S, NH and —(CH₂)$_x$—;
R¹, R² and R³ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;
o, p, q are independently selected from 0 or 1;
x is an integer between 1 and 10;
R⁴ is H or OH; and
R⁵ is H, OH or carbonyl.

15. The composition of any one of paragraphs 1-14, wherein at least one conjugate is a treatment or preventative composition for treating narcotic or opioid abuse or prevent withdrawal.

16. The composition of any one of paragraphs 1-14, wherein at least one conjugate is a pain treatment composition.

17. The composition of any one of paragraphs 1-14, wherein at least one conjugate is a moderate to severe pain treatment composition.

18. The composition of any one of paragraphs 1-14, wherein at least one conjugate reduces or prevents oral, intranasal or intravenous drug abuse.

19. The composition of any one of paragraphs 1-14, wherein at least one conjugate provides oral, intranasal or parenteral drug abuse resistance.

20. The composition of any one of paragraphs 1-14, wherein at least one conjugate exhibits a slower rate of release over time and a higher AUC when compared to unconjugated hydrocodone over that same time period.

21. The composition of any one of paragraphs 1-14, wherein at least one conjugate exhibits less variability in the oral PK profile when compared to unconjugated hydrocodone.

22. The composition of any one of paragraphs 1-14, wherein at least one conjugate has reduced side effects when compared with unconjugated hydrocodone.

23. The composition of any one of paragraphs 1-14, wherein at least one conjugate is resistant to drug tampering by either physical or chemical manipulation.

24. The composition of any one of paragraphs 1-14, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

25. The composition of any one of paragraphs 1-14, wherein at least one conjugate is provided in an amount sufficient to provide a therapeutically bioequivalent AUC when compared to unconjugated hydrocodone.

26. The composition of any one of paragraphs 1-14, wherein at least one conjugate is provided in an amount sufficient to provide a therapeutically bioequivalent AUC when compared to unconjugated hydrocodone but does not provide an equivalent $C_{max}$.

27. The composition of any one of paragraphs 1-14, wherein at least one conjugate is provided in an amount sufficient to provide a therapeutically bioequivalent AUC when compared to hydrocodone alone, but provides a higher $C_{max}$.

28. The composition of any one of paragraphs 1-14, wherein at least one conjugate is provided in an amount sufficient to provide a therapeutically bioequivalent AUC and $C_{max}$ when compared to hydrocodone alone.

29. The composition of any one of paragraphs 1-14, wherein at least one conjugate is present in an amount of from about 0.5 mg or higher.

30. The composition of any one of paragraphs 1-14, wherein at least one conjugate is present in an amount of from about 2.5 mg or higher.

31. The composition of any one of paragraphs 1-14, wherein at least one conjugate is present in an amount of from about 5 mg or higher.

32. The composition of any one of paragraphs 1-14, wherein at least one conjugate is present in an amount of from about 10 mg or higher.

33. The composition of any one of paragraphs 1-14, wherein at least one conjugate is present in an amount of from about 20 mg or higher.

34. The composition of any one of paragraphs 1-14, wherein at least one conjugate is present in an amount of from about 50 mg or higher.

35. The composition of any one of paragraphs 1-14, wherein at least one conjugate is present in an amount of from about 100 mg or higher.

36. The composition of any one of paragraphs 1-14, wherein at least one conjugate exhibits less variability in the intranasal PK profile when compared to unconjugated hydrocodone.

37. The composition of any one of paragraphs 1-14, wherein at least one conjugate exhibits less variability in the parenteral PK profile when compared to unconjugated hydrocodone.

38. The composition of any one of paragraphs 1-14, wherein at least one conjugate exhibits less variability in the intravenous PK profile when compared to unconjugated hydrocodone.

39. A method for treating a patient having a disease, disorder or condition requiring or mediated by binding of an opioid to the opioid receptors of the patient, comprising orally administering to the patient a pharmaceutically effective amount of at least one conjugate of hydrocodone and at least one of phenylethanoic acid, phenylpropanoic acid, phenylpropenoic acid, a salt thereof, a derivative thereof or a combination thereof.

40. A method for treating a patient having a disease, disorder or condition requiring or mediated by binding of an opioid to the opioid receptors of the patient, comprising orally administering to the patient a pharmaceutically effective amount of a phenylethanoate-hydrocodone conjugate, a salt thereof, a derivative thereof or a combination thereof, wherein the conjugate is ibuprofen-hydrocodone.

41. A method for treating a patient having a disease, disorder or condition requiring or mediated by binding of an opioid to the opioid receptors of the patient, comprising orally administering to the patient a pharmaceutically effective amount of a phenylpropenoate-hydrocodone conjugate, a salt thereof, a derivative thereof or a combination thereof, wherein the conjugate is cinnamate-hydrocodone.

42. A method for treating a patient having a disease, disorder or condition requiring or mediated by binding of an opioid to the opioid receptors of the patient, comprising orally administering to the patient a pharmaceutically effective amount of a phenylethanoate-hydrocodone conjugate, a salt thereof, a derivative thereof or a combination thereof, wherein the conjugate is naproxen-hydrocodone.

43. The method of any one of paragraphs 39-42, wherein at least one conjugate binds reversibly to the opioid receptors of the patient.

44. The method of any one of paragraphs 39-42, wherein at least one conjugate binds reversibly to the opioid receptors of the patient without a substantial CNS depressive effect.

45. The method of any one of paragraphs 39-42, wherein at least one conjugate prevents or reduces at least one constipatory side effect of hydrocodone alone.

46. The method of any one of paragraphs 39-42, wherein at least one conjugate exhibits reduced or prevented constipatory effects.

47. The method any one of paragraphs 39-42, wherein at least one conjugate binds irreversibly to the opioid receptors of the patient.

48. The method of paragraph 47, wherein at least one conjugate binds irreversibly to the opioid receptors of the patient without a CNS depressive effect.

49. A method for treating a patient having a disease, disorder or condition requiring inhibiting binding of an opioid to the opioid receptors of the patient, comprising orally administering to the patient a pharmaceutically effective amount of at least one conjugate of hydrocodone and at least one phenylethanoic acid, phenylpropanoic acid, phenylpropenoic acid, a salt thereof, a derivative thereof or a combination thereof.

50. A method for treating a patient having a disease, disorder or condition requiring inhibiting binding of an opioid to the opioid receptors of the patient, comprising orally administering to the patient a pharmaceutically effective amount of at least one phenylethanoate-hydrocodone conjugate, a salt thereof, a derivative thereof or a combination thereof, wherein the conjugate is ibuprofen-hydrocodone.

51. A method for treating a patient having a disease, disorder or condition requiring inhibiting binding of an opioid to the opioid receptors of the patient, comprising orally administering to the patient a pharmaceutically effective amount of at least one phenylpropenoate-hydrocodone conjugate, a salt thereof, a derivative thereof or a combination thereof, wherein the conjugate is cinnamate-hydrocodone.

52. A method for treating a patient having a disease, disorder or condition requiring inhibiting binding of the opioid receptors of the patient, comprising orally administering to the patient a pharmaceutically effective amount of at least one phenylethanoate-hydrocodone conjugate, a salt thereof, a derivative thereof or a combination thereof, wherein the conjugate is naproxen-hydrocodone.

53. The method of any one of paragraphs 49-52, wherein at least one conjugate reversibly inhibits binding of an opioid to the opioid receptor of the patient.

54. The method of any one of paragraphs 49-52, wherein at least one conjugate reversibly inhibits binding of an opioid to the opioid receptor of the patient without a substantial CNS depressive effect.

55. The method of any one of paragraphs 49-52, wherein at least one conjugate prevents or reduces at least one constipatory side effect of hydrocodone alone.

56. The method of paragraph 39 or 49, wherein the conjugate comprises at least one phenylethanoic acid, a salt thereof, a derivative thereof or a combination thereof having the formula I:

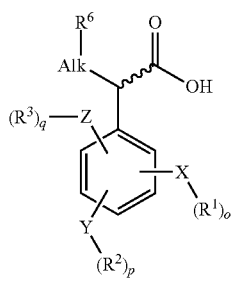

(I)

wherein,

X, Y and Z are independently selected from the group consisting of H, O, S, NH and —(CH$_2$)$_x$—;

R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

Alk is an alkyl chain —(CH$_2$)$_n$—, wherein n is 0 or 1; and

R$^6$ is H, OH or carbonyl.

57. The method of paragraph 39 or 49, wherein the conjugate comprises at least one phenylpropenoic acid, or phenylpropanoic acid, a salt thereof, a derivative thereof or a combination thereof having the formula II or formula III:

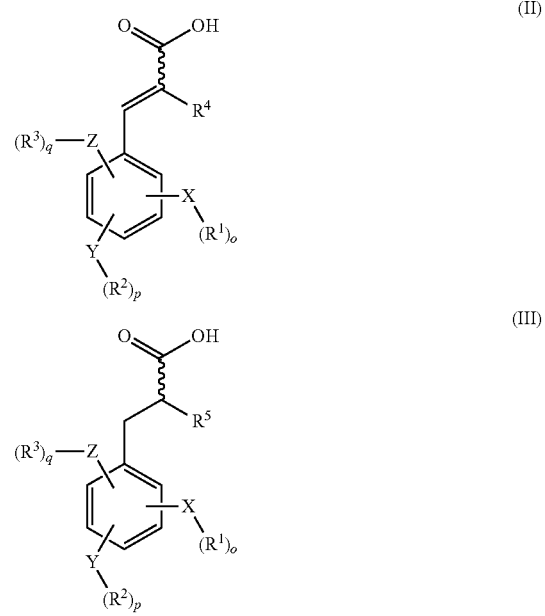

wherein,

X, Y and Z are independently selected from the group consisting of H, O, S, NH and —(CH$_2$)$_x$—;

R$^1$, R$^2$ and R$^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

R$^4$ is H or OH; and

R$^5$ is H, OH or carbonyl.

58. The method of any one of paragraphs 39-42 and 49-52, wherein at least one conjugate exhibits a slower rate of release over time when compared to an equivalent molar amount of unconjugated hydrocodone over that same time period.

59. The method of any one of paragraphs 39-42 and 49-52, wherein at least one conjugate exhibits a reduced AUC when compared to an equivalent molar amount of unconjugated hydrocodone over that same time period.

60. The method of any one of paragraphs 39-42 and 49-52, wherein at least one conjugate exhibits less variability in the oral PK profile when compared to an equivalent molar amount of unconjugated hydrocodone.

61. The method of any one of paragraphs 39-42 and 49-52, wherein at least one conjugate has reduced side effects when compared with an equivalent molar amount of unconjugated hydrocodone.

62. The method of any one of paragraphs 39-42 and 49-52, wherein at least one conjugate is provided in a dosage form selected from the group consisting of: a tablet, a capsule, a caplet, a suppository, a troche, a lozenge, an oral powder, a solution, an oral film, a thin strip, a slurry, and a suspension.

63. The method of any one of paragraphs 39-42 and 49-52, wherein at least one conjugate is provided in an amount sufficient to provide a therapeutically bioequivalent AUC when compared to an equivalent molar amount of unconjugated hydrocodone.

64. The method of any one of paragraphs 39-42 and 49-52, wherein at least one conjugate is provided in an amount sufficient to provide a therapeutically bioequivalent AUC and $C_{max}$ when compared to an equivalent molar amount of unconjugated hydrocodone.
65. The method of any one of paragraphs 39-42 and 49-52, wherein at least one conjugate is provided in an amount sufficient to provide a therapeutically bioequivalent AUC when compared to an equivalent molar amount of unconjugated hydrocodone, but does not provide an equivalent $C_{max}$.
66. The method of any one of paragraphs 39-42 and 49-52, wherein at least one conjugate is present in an amount of from about 0.5 mg or higher.
67. The method of any one of paragraphs 39-42 and 49-52, wherein at least one conjugate is present in an amount of from about 2.5 mg or higher.
68. The method of any one of paragraphs 39-42 and 49-52, wherein at least one conjugate is present in an amount of from about 5 mg or higher.
69. The method of any one of paragraphs 39-42 and 49-52, wherein at least one conjugate is present in an amount of from about 10 mg or higher.
70. The method of any one of paragraphs 39-42 and 49-52, wherein at least one conjugate is present in an amount of from about 20 mg or higher.
71. The method of any one of paragraphs 39-42 and 49-52, wherein at least one conjugate is present in an amount of from about 50 mg or higher.
72. The method of any one of paragraphs 39-42 and 49-52, wherein at least one conjugate is present in an amount of from about 100 mg or higher.
73. A pharmaceutical kit comprising:
a specified amount of individual doses in a package containing a pharmaceutically effective amount of at least one conjugate of hydrocodone and at least one of phenylethanoic acid, phenylpropanoic acid, phenylpropenoic acid, a salt thereof, a derivative thereof or a combination thereof.
74. The pharmaceutical kit of paragraph 73, wherein the conjugate comprises at least one phenylethanoic acid, a salt thereof, a derivative thereof or a combination thereof having the formula I:

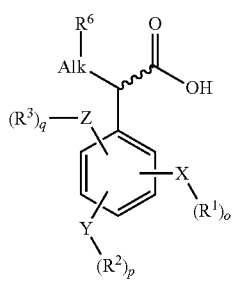

(I)

wherein,
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;
o, p, q are independently selected from 0 or 1;
x is an integer between 1 and 10;
Alk is an alkyl chain —$(CH_2)_n$—, wherein n is 0 or 1; and
$R^6$ is H, OH or carbonyl.

75. The pharmaceutical kit of paragraph 73, wherein the conjugate comprises at least one phenylpropenoic acid, phenylpropanoic acid, a salt thereof, a derivative thereof or a combination thereof having the formula II or formula III:

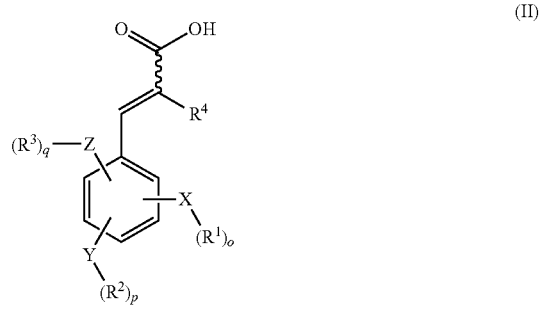

(II)

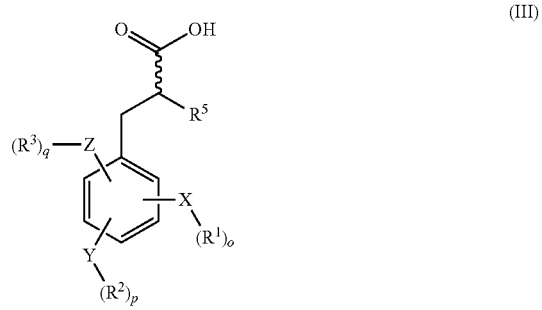

(III)

wherein,
X, Y and Z are independently selected from the group consisting of H, O, S, NH and —$(CH_2)_x$—;
$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;
o, p, q are independently selected from 0 or 1;
x is an integer between 1 and 10;
$R^4$ is H or OH; and
$R^5$ is H, OH or carbonyl.
76. The kit of paragraph 73, 74 or 75, wherein the kit further comprises: (ii) instructions for use of the kit in a method for treating or preventing drug withdrawal symptoms or pain in a human.
77. The kit of paragraph 76, wherein the patient is a pediatric patient.
78. The kit of paragraph 76, wherein the patient is an elderly patient.
79. The kit of paragraph 76, wherein the patient is a normative patient.
80. The kit of paragraph 73, 74 or 75, wherein the individual dosages comprise at least about 0.5 mg or higher of at least one conjugate.
81. The kit of paragraph 73, 74 or 75, wherein the individual dosages comprise at least about 2.5 mg or higher of at least one conjugate.
82. The kit of paragraph 73, 74 or 75, wherein the individual dosages comprise at least about 5.0 mg or higher of at least one conjugate.
83. The kit of paragraph 73, 74 or 75, wherein the individual dosages comprise at least about 10 mg or higher of at least one conjugate.
84. The kit of paragraph 73, 74 or 75, wherein the individual dosages comprise at least about 20 mg or higher of at least one conjugate.

85. The kit of paragraph 73, 74 or 75, wherein the individual dosages comprise at least about 50 mg or higher of at least one conjugate.

86. The kit of paragraph 73, 74 or 75, wherein the individual dosages comprise at least about 100 mg or higher of at least one conjugate.

87. The kit of paragraph 73, 74 or 75, wherein the kit comprises from about 1 to about 60 individual doses.

88. The kit of paragraph 73, 74 or 75, wherein the kit comprises from about 10 to about 30 individual doses.

89. The kit of paragraph 73, wherein at least one conjugate is ibuprofen-hydrocodone.

90. The kit of paragraph 73, wherein at least one conjugate is cinnamate-hydrocodone.

91. A prodrug comprising a conjugate of hydrocodone and at least one phenylethanoic acid, a salt thereof, a derivative thereof or a combination thereof having the formula I:

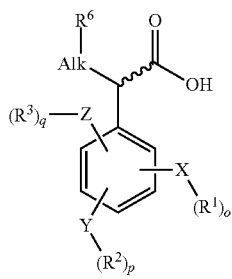
(I)

wherein,

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

Alk is an alkyl chain —$(CH_2)_n$—, wherein n is 0 or 1; and $R^6$ is H, OH or carbonyl.

92. A prodrug comprising a conjugate of hydrocodone and at least one of phenylpropanoic acid, phenylpropenoic acid, a salt thereof, a derivative thereof or a combination thereof having the formula II or formula III:

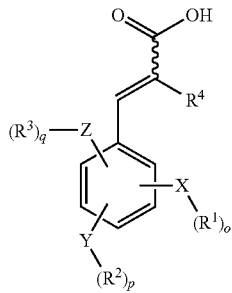
(II)

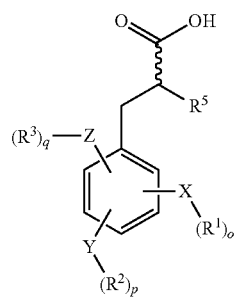
(III)

wherein,

X, Y and Z are independently selected from the group consisting of H, O, S, NH and —$(CH_2)_x$—;

$R^1$, $R^2$ and $R^3$ are independently selected from the group consisting of H, alkyl, alkoxy, aryl, alkenyl, alkynyl, halo, haloalkyl, alkylaryl, arylalkyl, heterocycle, aromatic, arylalkoxy, cycloalkyl, cycloalkenyl and cycloalkynyl;

o, p, q are independently selected from 0 or 1;

x is an integer between 1 and 10;

$R^4$ is H or OH; and $R^5$ is H, OH or carbonyl.

93. A prodrug comprising a phenylethanoate-hydrocodone conjugate, a phenylpropanoate-hydrocodone conjugate, a phenylpropenoate-hydrocodone conjugate, a derivative thereof or a combination thereof.

94. A prodrug comprising ibuprofen-hydrocodone.

95. A prodrug comprising cinnamate-hydrocodone.

96. A prodrug comprising naproxen-hydrocodone.

The presently described technology is now described in such full, clear, concise and exact terms as to enable any person skilled in the art to which it pertains, to practice the same. It is to be understood that the foregoing describes preferred embodiments of the technology and that modifications may be made therein without departing from the spirit or scope of the invention as set forth in the appended claims.

The invention claimed is:

1. A composition comprising a conjugate, wherein the conjugate is ibuprofen-hydrocodone (IBU-HC) having the following structure:

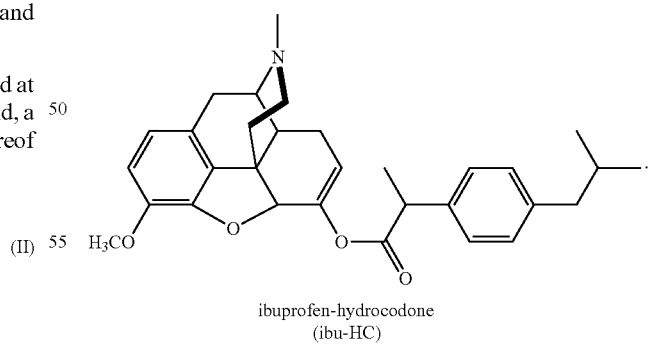

ibuprofen-hydrocodone
(ibu-HC)

2. The composition of claim 1, wherein the conjugate is a treatment composition for treating narcotic or opioid abuse or reduces withdrawal.

3. The composition of claim 1, wherein the least one conjugate reduces oral, intranasal or intravenous drug abuse.

4. The composition of claim 1, wherein the conjugate is a pain treatment composition.

5. The composition of claim 1, wherein the conjugate exhibits a slower rate of release over time and a higher AUC when compared to unconjugated hydrocodone over that same time period.

6. The composition of claim 1, wherein the conjugate exhibits less variability in the oral PK profile when compared to unconjugated hydrocodone.

7. The composition of claim 1, wherein the conjugate is provided in a dosage form selected from the group consisting of: a tablet, a capsule, a caplet, a suppository, a troche, a lozenge, an oral powder, a solution, an oral film, a thin strip, a slurry, and a suspension.

8. The composition of claim 1, wherein the conjugate is provided in an amount sufficient to provide a therapeutically bioequivalent AUC when compared to unconjugated hydrocodone.

9. The composition of claim 1, wherein the conjugate is provided in an amount sufficient to provide a therapeutically bioequivalent AUC and $C_{max}$ when compared to unconjugated hydrocodone.

10. The composition of claim 1, wherein the conjugate is provided in an amount sufficient to provide a therapeutically bioequivalent AUC when compared to unconjugated hydrocodone but does not provide an equivalent $C_{max}$.

* * * * *